US010508289B2

(12) United States Patent
Duchateau et al.

(10) Patent No.: US 10,508,289 B2

(45) Date of Patent: Dec. 17, 2019

(54) RARE-CUTTING ENDONUCLEASES FOR EFFICIENT AND SPECIFIC TARGETING DNA SEQUENCES COMPRISING HIGHLY REPETITIVE MOTIVES

(71) Applicant: CELLECTIS, S.A., Paris (FR)

(72) Inventors: Philippe Duchateau, Draveil (FR); Alexandre Juillerat, Paris (FR)

(73) Assignee: CELLECTIS, Paris (FR)

( * ) Notice: Subject to any disclaimer, the term of this patent is extended or adjusted under 35 U.S.C. 154(b) by 0 days.

(21) Appl. No.: 15/031,996

(22) PCT Filed: Oct. 24, 2014

(86) PCT No.: PCT/EP2014/072833

§ 371 (c)(1),
(2) Date: Apr. 25, 2016

(87) PCT Pub. No.: WO2015/059265

PCT Pub. Date: Apr. 30, 2015

(65) Prior Publication Data

US 2016/0273002 A1 Sep. 22, 2016

(30) Foreign Application Priority Data

Oct. 25, 2013 (DK) ................................ 2013 70623

(51) Int. Cl.

*C12N 15/90* (2006.01)
*C12N 9/22* (2006.01)
*A61K 48/00* (2006.01)
*C07K 14/195* (2006.01)
*A61K 38/00* (2006.01)

(52) U.S. Cl.

CPC .......... *C12N 15/907* (2013.01); *A61K 48/005* (2013.01); *C07K 14/195* (2013.01); *C12N 9/22* (2013.01); *C12Y 301/21004* (2013.01); *A61K 38/00* (2013.01); *A61K 48/00* (2013.01); *C07K 2319/80* (2013.01); *C12Y 301/00* (2013.01)

(58) Field of Classification Search

None

See application file for complete search history.

(56) References Cited

U.S. PATENT DOCUMENTS 8,841,260 B2 * 9/2014 Miller .................. C12N 15/907 424/93.21

FOREIGN PATENT DOCUMENTS

WO 2012/093833 A2 7/2012
WO 2013/068845 A2 5/2013

OTHER PUBLICATIONS

Edgell, D.R. et al., "Coincidence of Cleavage Sites on Intron Endonuclease I-Tevl and Critical Sequences of the Host Thymidylate Synthase Gene" J. Mol. Biol. (2004); vol. 343:5; pp. 1231-1241.

Kleinstiver, B.P. et al., "Monomeric Site-Specific Nucleases for Genome Editing"; PNAS (2012); vol. 109:21; pp. 8061-8066.

Liu, Q. et al., "Role of the Interdomain Linker in Distance Determination for Remote Cleavage by Homing Endonuclease I-Tel", J. Mol. Biol. (2008); vol. 379:5; pp. 1094-1106.

Lixin, L. et al., "Rapid and Highly Efficient Construction of TALE-Based Transcriptional Regulators and Nucleases for Genome Modification", Plant Mol. Biol. (2012); vol. 78:4-5; pp. 407-416.

Miller, J. et al., A TALE Nuclease Architecture for Efficient Genome Editing, Nat. Biotech. (2011); vol. 29:2; pp. 143-148.

Mitteleman, D. et al., "Zinc-Finger Directed Double-Strand Breaks Within CAG Repeat Tracts Promote Repeat Instability in Human Cells", PNAS (2009); vol. 106:24; pp. 9607-9612.

Morbitzer, R. et al., "Assembly of Custom TALE-Type DNA Binding Domains by Modular Cloning": NAR (2011); vol. 39:13; pp. 5790-5799.

* cited by examiner

*Primary Examiner* — Richard G Hutson

(74) *Attorney, Agent, or Firm* — Arrigo, Lee, Guttman & Mouta-Bellum LLP

(57) ABSTRACT

The present invention is in the field of genetic editing tools and methods of genetic engineering. It relates to the engineering of rare-cutting endonucleases designed to contract highly repetitive motives in chromosomes, which are at the origin of certain genetic diseases, in particular the so-called "triplet repeat diseases", such as the Huntington disease. The invention encompasses the method for contracting the repetitive motives, the rare-cutting endonucleases for use to contract repetitive motives in a gene subjected to repeat disorder, the polynucleotides and vectors encoding thereof as well as the resulting pharmaceutical compositions.

6 Claims, 4 Drawing Sheets

Specification includes a Sequence Listing.

RARE-CUTTING ENDONUCLEASES FOR EFFICIENT AND SPECIFIC TARGETING DNA SEQUENCES COMPRISING HIGHLY REPETITIVE MOTIVES

FIELD OF THE INVENTION

The present invention is in the field of genetic editing tools and use thereof. It relates to the engineering of rare-cutting endonucleases designed to contract highly repetitive motives in chromosomes, which are at the origin of certain genetic diseases, in particular the so-called "triplet repeat diseases", such as the Huntington disease. The invention encompasses the method for contracting the repetitive motives, the rare-cutting endonucleases for use to contract repetitive motives in a gene subjected to repeat disorder, the polynucleotides and vectors encoding thereof as well as the resulting pharmaceutical compositions.

BACKGROUND OF THE INVENTION

Since the early 1990s, expansion of unstable nucleotide (microsatellite) repeats, notably trinucleotide repeat was identified as a novel mutational mechanism underlying certain human diseases. Over the years, several additional developmental and neuromuscular disorders were identified to be caused by either an insertion or a duplication of trinucleotide repeats as well as unstable tetra-, penta-, hexa-nucleotide, and longer repeats (Mirkin 2007). This insertion or duplication of polynucleotide repeats can induce a protein loss of function, a RNA toxic gain of function or a protein toxic gain of function leading to the disorder. Examples of such disorders include Huntington disease, inherited ataxias, fragile X syndrome, myotonic dystrophy a common genetic muscular dystrophy, a group of dominantly inherited ataxias, and most recently an unstable hexanucleotide repeat in the C9ORF72 gene as a frequent cause of frontotemporal dementia/amyotrophic lateral sclerosis (DeJesus-Hernandez, Mackenzie et al. 2011; Renton, Majounie et al. 2011) (see for review (Nelson, Orr et al. 2013)).

Treatment options for most of repeat expansion disorders are very limited. One of the most attractive therapeutic strategies envisaged for various neurodegenerative diseases is gene therapy. Indeed, several strategies to turn off expression of repeat expanded have been developed. In particular, silencing the mutant gene using RNA interference technology within cell has been realized for preventing the toxic function of the protein or RNA (Wang, Liu et al. 2005; Machida, Okada et al. 2006; DiFiglia, Sena-Esteves et al. 2007). However, basically the design of RNA interference does not allow the distinction between the normal and repeat expansion sequences and induce simultaneous reduction of both the mutant and wild type gene (Caplen, Taylor et al. 2002). However, the huntingtin protein is widely expressed and is required for neuronal function and survival in the brain (Duyao, Auerbach et al. 1995; Dragatsis, Levine et al. 2000). Thus, it is important to reduce specifically expression of the mutant gene, while leaving the expression of the wild type protein unaffected.

Recently, Zinc Finger proteins were designed to bind poly-trinucleotides repeat of the huntingtin gene, responsible for the Huntington disease. Zinc fingers were concatenated into long chains with appropriate linker to obtain an optimal configuration for repressing preferably the repeat expanded huntingtin gene compared with the shorter repeats. This strategy allows more efficient repression of mutant gene expression compared to wild type gene. However it has not been known whether the repression would be sufficient to reduce protein levels for gene therapy (Garriga-Canut, Agustin-Pavon et al., International application: WO2013/130824).

A previous study (Richard, Dujon et al. 1999) has suggested that Induction of a cleavage event within the repeat sequence was associated with contraction of trinucleotide repeat arrays, which may be explained by two different mechanisms: (1) the two ends of the break are available to invade the template, but they can invade at any location within the template, since they carry repeated sequences that are homologous to the template; or (2) only one end invades the template and the newly synthesized strand is displaced from its template, but can anneal with the other end containing repeats (Richard, Dujon et al. 1999). However, due to the highly frequency of repeat sequences within the genome, engineered DNA binding nuclease designed to be specific to said repeat sequences, are likely to induce off-site mutagenesis at several positions throughout the human genome. Consequently, the ability to create a cleavage in the repeat sequence only at the desired genomic position would be highly desirable.

To overcome the above limitations, the present inventors have developed a genetic therapeutic strategy to decrease the number of expanded polynucleotide repeats by using DNA binding nucleases, while maintaining the integrity of the genome and functionality of the corrected gene. This strategy mainly relies on the design of the DNA binding nucleases along with the selection of genome sequences to specifically target the repeat sequence associated with the triplet repeat disorders.

SUMMARY OF THE INVENTION

In a general aspect, the present invention relates to a rare-cutting endonuclease for use to contract polynucleotide repeats, preferably in a specific gene subjected to repeat disorder. In particular, the rare-cutting endonuclease is engineered to specifically cleave repeated sequences, characterized in that said rare-cutting endonuclease recognizes a target sequence comprising a region adjacent to the repeat sequence. The present invention relates to a method of engineering a rare-cutting endonuclease used to induce contraction within highly repetitive motives in a specific region. Preferably, said rare-cutting endonuclease targets a sequence comprising the region adjacent to the repeat sequence, such that the rare-cutting endonuclease specifically binds the selected target sequence and cleaves the repeat sequence. Cleavage of the repeat sequence induces a repairing process conducting to the contraction of the repeat sequence within the specific gene and thus the decrease of the expanded repeat sequence to an approximately wild type configuration. Preferably, said rare-cutting endonuclease is a Cas9-guide RNA complex which specifically cleaves a repeat sequence characterized in that the guide RNA hybridizes a target sequence comprising a region adjacent to the repeat sequence. Preferably, said rare-cutting endonuclease is a modular DNA binding nuclease, which comprises a DNA binding domain such as TALE, MBBBD, Zinc Finger (ZF) domain fused a catalytic domain of an endonuclease. Said DNA binding nuclease can act as a monomer or a dimer. The dimeric DNA binding nuclease comprises a first DNA binding domain capable of binding a sequence adjacent to the repeat sequence fused to a nuclease catalytic domain and a second DNA binding domain capable of binding repeat sequence fused to a nuclease catalytic domain (see FIG. 1). Said nuclease catalytic domain which acts as a dimer is preferably FokI catalytic domain. The rare-cutting endonuclease of the present invention is particularly suitable for treating or preventing repeat disease, such as Huntington disease, by contracting the highly repetitive motives region.

DESCRIPTION OF THE INVENTION

Figure 1:
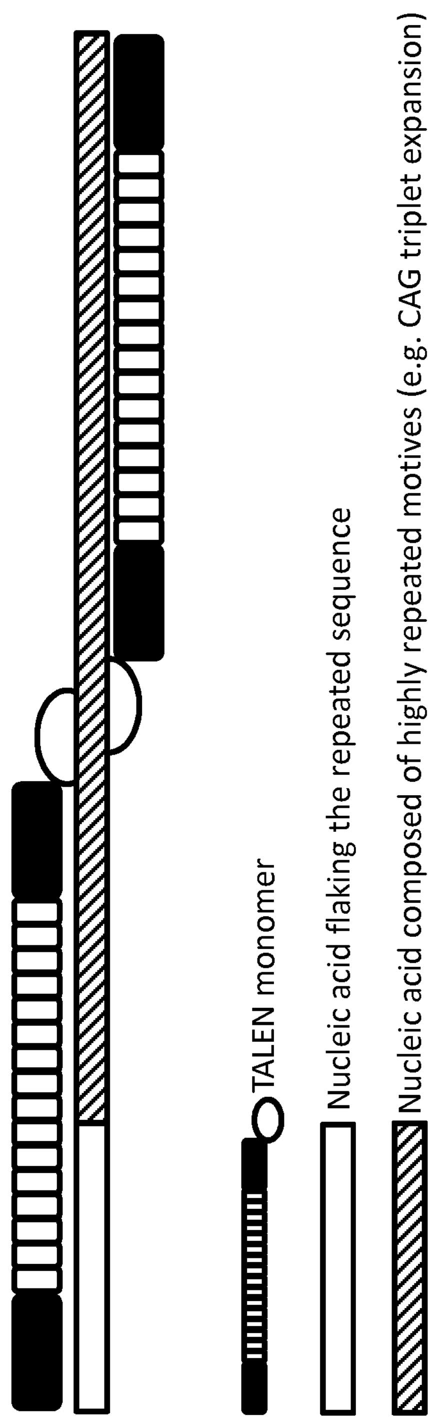
FIG. 1: A schematic representation of a TALE-nuclease engineered to specifically cleave a repeat sequence.

Unless specifically defined herein, all technical and scientific terms used have the same meaning as commonly understood by a skilled artisan in the fields of gene therapy, biochemistry, genetics, and molecular biology.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, New York: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

Engineered Rare-Cutting Endonucleases for Use to Contract Polynucleotide Repeats The present invention relates to a rare-cutting endonuclease which is capable of specifically recognizing and cleaving a repeat sequence. To avoid off-site targeting, the inventors engineered a rare-cutting endonuclease to specifically cleave repeated sequence, characterized in that said rare-cutting endonuclease recognizes a target sequence comprising a region adjacent to the repeat sequence. The cleavage of the repeat sequence induces a repairing process conducting to the contraction of polynucleotide repeats, preferably present in a gene subjected to repeat disorder. In a particular embodiment, the present invention relates to a method of engineering a rare-cutting endonuclease which specifically cleaves a repeat sequence. In particular, said method comprises the steps of: (a) selecting a target sequence comprising a region adjacent to the repeat sequence; (b) engineering a rare-cutting endonuclease capable of recognizing said target sequence and cleaving the repeat sequence.

The target sequence according to the present invention can be present in a chromosome, an episome, an organellar genome such as mitochondrial or chloroplast genome or genetic material that can exist independently to the main body of genetic material such as an infecting viral genome, plasmids, episomes, transposons for example. A target nucleic acid sequence can be within the coding sequence of a gene, within transcribed non-coding sequence such as, for example, leader sequences, trailer sequence or introns, or within non-transcribed sequence, either upstream or downstream of the coding sequence. The nucleic acid target sequence is defined by the 5' to 3' sequence of one strand of said target. In particular the target sequence comprises a part of the repeat sequence and a sequence adjacent thereto.

The repeat sequence can be trinucleotide repeats, but also tetra-, penta- or hexa-nucleotides. As non limiting examples, said repeat sequence can be (CGC)n, (GAA)n, (CTG)n, (CCTG)n, (CGG)n, (ATTCT)n, (CAG)n wherein n can be comprised between 1 to 20000, preferably between 10 to 15000, preferably more than 20 (see for review: (Orr and Zoghbi 2007)). Said target sequence comprises a part of a repeat sequence comprising at least 3, preferably at least 4, 5, 6, 7, 8, 9, 10 nucleotides.

The region adjacent to the repeat sequence needs to be sufficiently long to be specifically recognized by the rare-cutting endonuclease. The region adjacent to the repeat sequence comprises at least 5 nucleotides, preferably at least 6, 7, 8, 9, 10, 11, 12, 15 nucleotides. In a more preferred embodiment said adjacent sequence comprises between 5 and 10 nucleotides. The adjacent sequence can be in the 5' or the 3' region to the repeat sequence. Said target sequence is preferably within a genetic sequence in which expansion of unstable repeats can cause neurological disorder. As non limiting example, said genetic sequence can be selected from the group consisting of: 5'untranslated region (UTR) sequence of Fragile X mental retardation 1 gene (FMR1, MIM number: 309550, NG_007529.1) comprising (CGG)n repeat units; 5' UTR sequence of Fragile X mental retardation 2 gene (FMR2, MIM number 300806, NG_016313.1) comprising (CCG)n repeat units, the first intron of the Friedreich ataxia 1 gene (FRDA, MIM number: 606829, NG_008845.2) comprising (GAA)n repeat unit; 3'UTR sequence of dystrophia myotonica-protein kinase gene (DMPK, MIM number 605377, NG_009784.1) comprising (CTG)n repeat units; the first intron of the Zing finger 9 gene (ZNF9, MIM number: 602668, NG_011902.1) comprising (CCTG)n repeat units; Ataxin 8 (ATXN8, MIM number: 613289, GenBank: DQ641254.1) comprising (CAG)n repeat units; Ataxin 8 opposite strand (ATXN8OS, MIM number: 603680, NR_002717.2) comprising (CTG)n repeat units, intron 9 of the ataxin 10 gene (ATXN10, MIM number: 611150, NG_016212.1) comprising (CAGT)n repeat units; 5' UTR sequence of protein phosphatase 2 regulatory subunit B beta gene (PPP2R2B, MIM number: 604325, NG_011570.1) comprising (CAG)n repeat units; N-terminus of the huntingtin gene (HTT, MIM number: 613004, NG_009378.1) comprising (CAG)n repeat units; ataxin 1 (ATXN1, MIM number: 601556, NG_011571.1) comprising (CAG)n repeat units; ataxin 2 (ATXN2; MIM number: 601517, NG_011572.1) comprising (CAG)n repeat; ataxin 3 (ATXN3, MIM number: 607047, NG_008198.1) comprising (CAG)n repeat units; the exon 47 of Calcium Channel, voltage-dependent, P/Q type, alpha-1A subunit gene (CACNA1A, MIM number: 601011, NC_000019.9) comprising (CAG)n repeat units; ataxin 7 (ATXN7, MIM number: 607640, NG_008227.1) comprising (CAG)n repeat units; TATA box-binding protein gene (TBP, MIM number: 60075, NG_008165.1) comprising a (CAG)n and/or (CAA)n repeat units; the exon 1 of spinal and Androgen receptor gene (AR, MIM number: 313700, NG_009014.2) comprising (CAG)n repeat units; atrophin 1 gene (ATN1, MIM number: 607462, NG_008047.1) comprising (CAG)n repeat units and homologue thereof.

In a more preferred embodiment, said target sequence is selected within the sequence encoding huntinting protein (SEQ ID NO: 1), preferably within sequence encoding the N-terminal part of the huntingtin protein (SEQ ID NO: 2), more preferably the target sequence is selected within the sequence SEQ ID NO: 3.

By “rare-cutting endonuclease”, it is meant any wild type or variant enzyme capable of catalyzing the hydrolysis (cleavage) of bonds between nucleic acids within a DNA or RNA molecule, preferably a DNA molecule. A rare-cutting endonucelase is highly specific, recognizing nucleic acid target sites ranging from 10 to 45 base pairs (bp) in length, usually ranging from 10 to 35 base pairs in length. The endonuclease according to the present invention recognizes and cleaves nucleic acid at specific polynucleotide sequences, further referred to as “target sequence”. The rare-cutting endonuclease can recognize and generate a single- or double-strand break at specific polynucleotides sequences.

Figure 4:
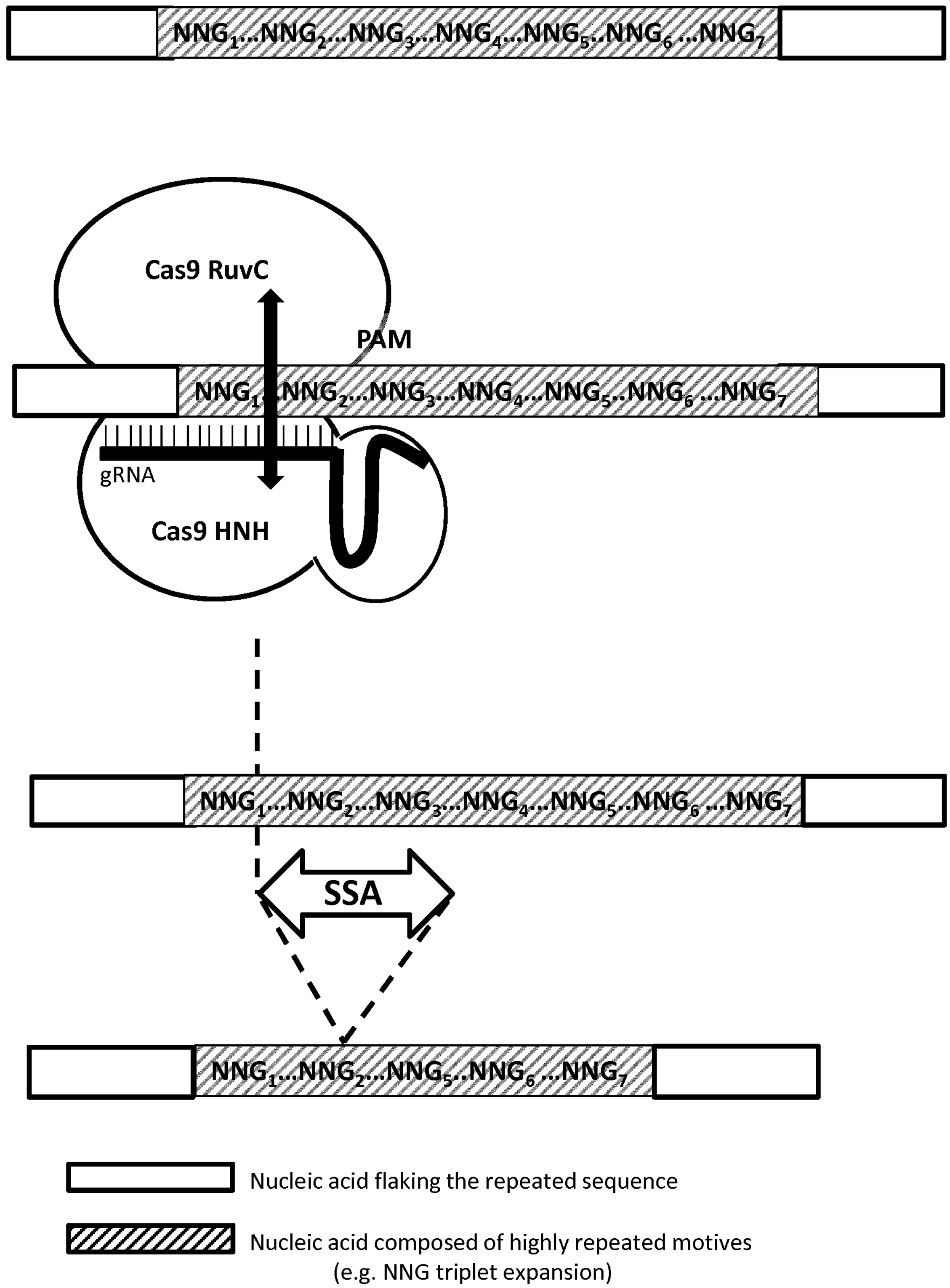
FIG. 4: A schematic representation of the use of Cas9-guide RNA complex engineered to specifically cleave a repeat sequence. The guide RNA is engineered to specifically recognize a target sequence comprising a region adjacent to the repeat sequence such that the Cas9-guide RNA complex cleaves the repeat sequence. The cleavage of the repeat sequence induces a repair process, such as single-strand annealing (SSA) process resulting in the contraction of the repeats.

The rare-cutting endonuclease according to the present invention can be a Cas9 endonuclease. Recently, a new genome engineering tool has been developed based on the RNA-guided Cas9 nuclease (Gasiunas, Barrangou et al. 2012; Jinek, Chylinski et al. 2012; Cong, Ran et al. 2013; Mali, Yang et al. 2013) from the type II prokaryotic CRISPR (Clustered Regularly Interspaced Short palindromic Repeats) adaptive immune system (see for review (Sorek, Lawrence et al. 2013)). The CRISPR Associated (Cas) system was first discovered in bacteria and functions as a defense against foreign DNA, either viral or plasmid. CRISPR-mediated genome engineering first proceeds by the selection of target sequence often flanked by a short sequence motif, referred as the proto-spacer adjacent motif (PAM). Following target sequence selection, a specific crRNA, complementary to this target sequence is engineered. Trans-activating crRNA (tracrRNA) required in the CRISPR type II systems paired to the crRNA and bound to the provided Cas9 protein. Cas9 acts as a molecular anchor facilitating the base pairing of tracRNA with cRNA (Deltcheva, Chylinski et al. 2011). In this ternary complex, the dual tracrRNA:crRNA structure acts as guide RNA that directs the endonuclease Cas9 to the cognate target sequence. In the present invention the guide RNA can hybridize the target sequence which comprises a region adjacent to the repeat sequence. Target recognition by the Cas9-tracrRNA:crRNA complex is initiated by scanning the target sequence for homology between the target sequence and the crRNA. In addition to the target sequence-crRNA complementarity, DNA targeting requires the presence of a short motif adjacent to the protospacer (protospacer adjacent motif—PAM). Following pairing between the dual-RNA and the target sequence, Cas9 subsequently introduces a blunt double strand break 3 bases upstream of the PAM motif (Garneau, Dupuis et al. 2010). According to the present invention, following the hybridization of the dual-RNA (guide RNA) and the target sequence which comprises a region adjacent to the repeat sequence, Cas9 cleaves repeated sequence (see FIG. 4).

Rare-cutting endonuclease can also be a homing endonuclease, also known under the name of meganuclease. Such homing endonucleases are well-known to the art (Stoddard 2005). Homing endonucleases recognize a DNA target sequence and generate a single- or double-strand break. Homing endonucleases are highly specific, recognizing DNA target sites ranging from 12 to 45 base pairs (bp) in length, usually ranging from 14 to 40 bp in length. The homing endonuclease according to the invention may for example correspond to a LAGLIDADG endonuclease, to a HNH endonuclease, or to a GIY-YIG endonuclease. Preferred homing endonuclease according to the present invention can be an I-CreI variant. A “variant” endonuclease, i.e. an endonuclease that does not naturally exist in nature and that is obtained by genetic engineering or by random mutagenesis can bind DNA sequences different from that recognized by wild-type endonucleases (see international application WO2006/097854).

Said rare-cutting endonuclease can be a modular DNA binding nuclease or a chimeric endonuclease. By chimeric endonuclease or modular DNA binding nuclease is meant any fusion proteins comprising at least one catalytic domain of an endonuclease and at least one DNA binding domain or protein specifying a nucleic acid target sequence.

The DNA binding domain is generally a RNA or DNA-binding domain formed by an independently folded polypeptide protein domain that contains at least one motif that recognizes double- or single-stranded polynucleotides. Said nucleic acid binding domain preferably recognizes a specific nucleic acid sequence named target sequence. Many such polypeptides have been described in the art having the ability to bind specific nucleic acid sequences. Such binding domains often comprise, as non limiting examples, helix-turn helix domains, leucine zipper domains, winged helix domains, helix-loop-helix domains, HMG-box domains, Immunoglobin domains, B3 domain or engineered zinc finger domain.

According to a preferred embodiment of the invention, the DNA binding domain is derived from a Transcription Activator like Effector (TALE), wherein sequence specificity is driven by a series of 33-35 amino acids repeats originating from *Xanthomonas* or *Ralstonia* bacterial proteins. These repeats differ essentially by two amino acids positions that specify an interaction with a base pair (Boch, Scholze et al. 2009; Moscou and Bogdanove 2009). Each base pair in the DNA target is contacted by a single repeat, with the specificity resulting from the two variant amino acids of the repeat (the so-called repeat variable dipeptide, RVD). TALE binding domains may further comprise an N-terminal translocation domain responsible for the requirement of a first thymine base ($T_0$) of the targeted sequence and a C-terminal domain that containing a nuclear localization signals (NLS). A TALE nucleic acid binding domain generally corresponds to an engineered core TALE scaffold comprising a plurality of TALE repeat sequences, each repeat comprising a RVD specific to each nucleotides base of a TALE recognition site. In the present invention, each TALE repeat sequence of said core scaffold is made of 30 to 42 amino acids, more preferably 33 or 34 wherein two critical amino acids (the so-called repeat variable dipeptide, RVD) located at positions 12 and 13 mediates the recognition of one nucleotide of said TALE binding site sequence; equivalent two critical amino acids can be located at positions other than 12 and 13 specially in TALE repeat sequence taller than 33 or 34 amino acids long. Preferably, RVDs associated with recognition of the different nucleotides are HD for recognizing C, NG for recognizing T, NI for recognizing A, NN for recognizing G or A. In another embodiment, critical amino acids 12 and 13 can be mutated towards other amino acid residues in order to modulate their specificity towards nucleotides A, T, C and G and in particular to enhance this specificity. By other amino acid residues is intended any of the twenty natural amino acid residues or unnatural amino acids derivatives.

A TALE nucleic acid binding domain usually comprises between 8 and 30 TALE repeat sequences. More preferably, said core scaffold of the present invention comprises between 8 and 20 TALE repeat sequences; again more preferably 15 TALE repeat sequences. It can also comprise an additional single truncated TALE repeat sequence made of 20 amino acids located at the C-terminus of said set of TALE repeat sequences, i.e. an additional C-terminal half-TALE repeat sequence. The TALE nucleic acid binding domains according to the present invention preferably comprise the nucleic acid sequences selected from the group consisting of SEQ ID NO: 4 and SEQ ID NO: 5. In another embodiment, said engineered TALE binding domain comprises a nucleic acid sequence having at least 80%, more preferably 90%, again more preferably 95% identity with the nucleic acid sequences selected from the group consisting of SEQ ID NO: 4 and SEQ ID NO: 5.

Other engineered DNA binding domains are modular base-per-base specific nucleic acid binding domains (MBBBD) (PCT/US2013/051783). Said MBBBD can be engineered, for instance, from the newly identified proteins, namely EAV36_BURRH, E5AW43_BURRH, E5AW45_BURRH and E5AW46_BURRH proteins from the recently sequenced genome of the endosymbiont fungi *Burkholderia Rhizoxinica* (Lackner, Moebius et al. 2011). MBBBD proteins comprise modules of about 31 to 33 amino acids that are base specific. These modules display less than 40% sequence identity with *Xanthomonas* TALE common repeats, whereas they present more polypeptides sequence variability. When they are assembled together, these modular polypeptides can although target specific nucleic acid sequences in a quite similar fashion as *Xanthomonas* TAL-nucleases.

According to a preferred embodiment of the present invention, said DNA binding domain is an engineered MBBBD binding domain comprising between 10 and 30 modules, preferably between 16 and 20 modules. The different domains from the above proteins (modules, N and C-terminals) from *Burkholderia* and *Xanthomonas* are useful to engineer new proteins or scaffolds having binding properties to specific nucleic acid sequences. In particular, additional N-terminal and C-terminal domains of engineered MBBBD can be derived from natural TALE like AvrBs3, PthXo1, AvrHah1, PthA, Tal1c as non-limiting examples.

Figure 2:
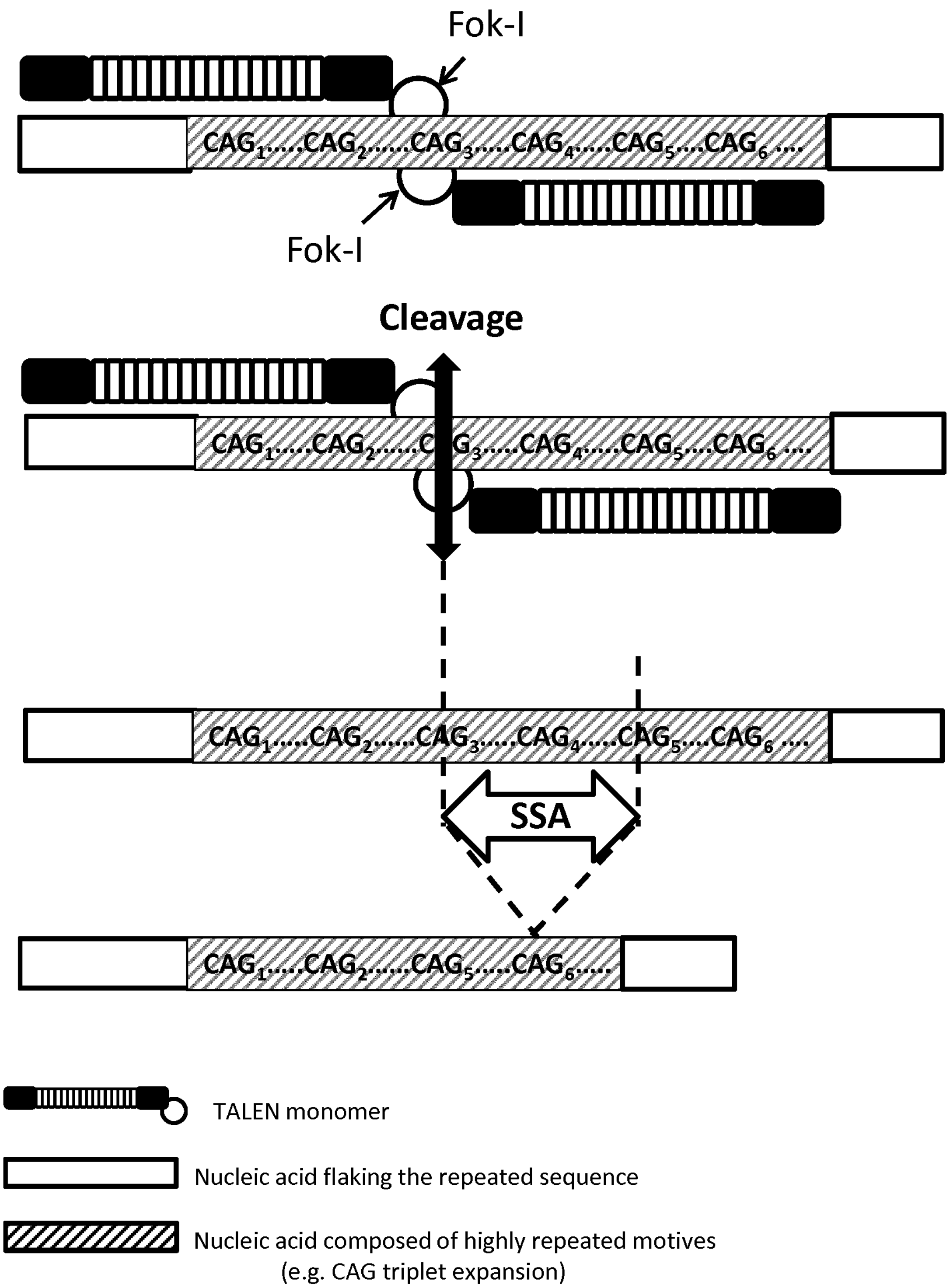
FIG. 2: A schematic representation of the use of dimeric TALE-nuclease engineered to specifically cleave a repeat sequence. One TALE-nuclease half-domain is engineered to recognize a target sequence comprising a region adjacent to the repeat sequence and another TALE-nuclease half-domain is engineered to recognize a target sequence within the repeat sequence such as the dimeric TALE-nuclease cleaves the repeat sequence. The cleavage of the repeat sequence induces a repair process, such as single-strand annealing (SSA) process resulting in the contraction of the repeats.
Figure 3:
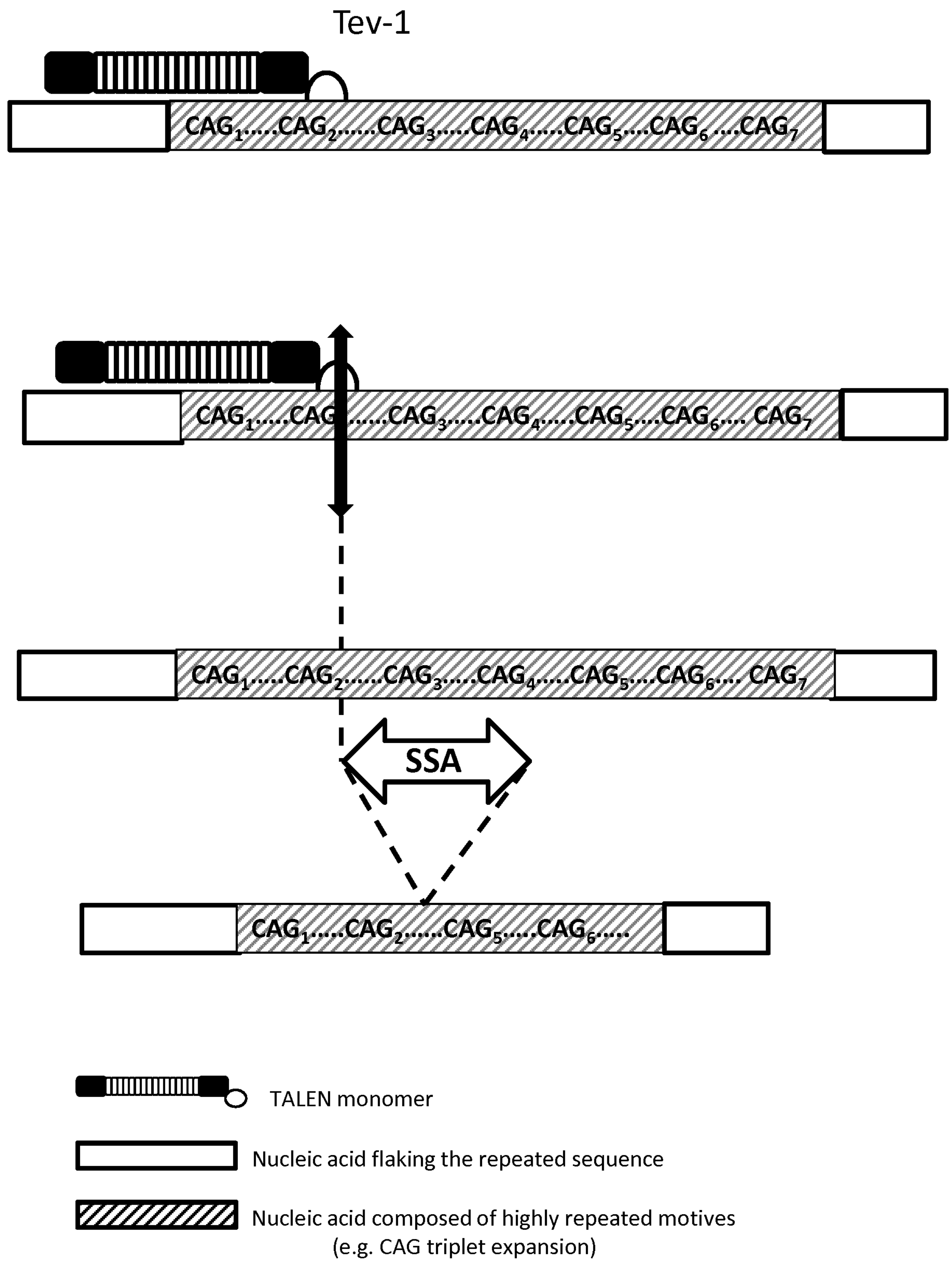
FIG. 3: A schematic representation of the use of monomeric TALE-nuclease engineered to specifically cleave a repeat sequence. Monomeric TALE-nuclease engineered specifically to cleave a repeat sequence, recognizes a target sequence comprising a region adjacent to the repeat sequence. The cleavage of the repeat sequence induces a repair process, such as single-strand annealing (SSA) process resulting in the contraction of the repeats.

"TALE-nuclease" or "MBBBD-nuclease" refers to engineered proteins resulting from the fusion of a DNA binding domain typically derived from Transcription Activator like Effector proteins (TALE) or MBBBD binding domain, with an endonuclease catalytic domain. Such catalytic domain is preferably a nuclease domain and more preferably a domain having endonuclease activity, like for instance I-TevI, ColE7, NucA and Fok-I. In a particular embodiment, said nuclease is a monomeric TALE-Nuclease or MBBBD-nuclease. A monomeric Nuclease is a nuclease that does not require dimerization for specific recognition and cleavage, such as the fusions of engineered DNA binding domain with the catalytic domain of I-TevI described in WO2012138927 (see FIG. 3). In another particular embodiment, said rare-cutting endonuclease is a dimeric TALE-nuclease or MBBBD-nuclease, preferably comprising a DNA binding domain fused to FokI (see FIG. 1). Said dimeric nuclease comprises a first DNA binding nuclease capable of binding a target sequence comprising a region adjacent to the repeat sequence and a second DNA binding nuclease capable of binding a target sequence within the repeat sequence, such that the dimeric nuclease induces a cleavage event within the repeat sequence (see FIG. 2). TALE-nuclease have been already described and used to stimulate gene targeting and gene modifications (Boch, Scholze et al. 2009; Moscou and Bogdanove 2009; Christian, Cermak et al. 2010). Such engineered TALE-nucleases are commercially available under the trade name TALEN™ (Cellectis, 8 rue de la Croix Jarry, 75013 Paris, France).

In another aspect, the present invention also relates to the rare-cutting endonucleases disclosed here, preferably rare-cutting endonucleases obtainable by the method described above. In a preferred embodiment, the present invention relates to the rare-cutting endonuclease which has at least 70%, preferably 80%, 85%, 90%; 95% identity with the amino acid sequence selected from the group consisting of: SEQ ID NO: 8, SEQ ID NO: 10 and SEQ ID NO: 15.

Polynucleotides, Vectors:

The present invention also relates to polynucleotides, vectors encoding the above described rare-cutting endonuclease according to the invention. In a preferred embodiment, the present invention relates to a polynucleotide comprising the nucleic acid sequence selected from the group consisting of: SEQ ID NO: 9, SEQ ID NO: 11 and SEQ ID NO: 16. In a preferred embodiment, the polynucleotide has at least 70%, preferably at least 80%, more preferably at least 90%, 95% 97% or 99% sequence identity with nucleic acid sequence selected from the group consisting of SEQ ID NO: 9, SEQ ID NO: 11 and SEQ ID NO: 16.

The polynucleotide may consist in an expression cassette or expression vector (e.g. a plasmid for introduction into a bacterial host cell, or a viral vector such as a baculovirus vector for transfection of an insect host cell, or a plasmid or viral vector such as a lentivirus for transfection of a mammalian host cell).

In a particular embodiment, the different nucleic acid sequences can be included in one polynucleotide or vector which comprises a nucleic acid sequence encoding ribosomal skip sequence such as a sequence encoding a 2A peptide. 2A peptides, which were identified in the Aphthovirus subgroup of picornaviruses, causes a ribosomal "skip"

from one codon to the next without the formation of a peptide bond between the two amino acids encoded by the codons (see (Donnelly and Elliott 2001; Donnelly, Luke et al. 2001; Atkins, Wills et al. 2007; Doronina, Wu et al. 2008)). By "codon" is meant three nucleotides on an mRNA (or on the sense strand of a DNA molecule) that are translated by a ribosome into one amino acid residue. Thus, two polypeptides can be synthesized from a single, contiguous open reading frame within an mRNA when the polypeptides are separated by a 2A oligopeptide sequence that is in frame. Such ribosomal skip mechanisms are well known in the art and are known to be used by several vectors for the expression of several proteins encoded by a single messenger RNA.

Those skilled in the art will recognize that, in view of the degeneracy of the genetic code, considerable sequence variation is possible among these polynucleotide molecules. Preferably, the nucleic acid sequences of the present invention are codon-optimized for expression in mammalian cells, preferably for expression in human cells. Codon-optimization refers to the exchange in a sequence of interest of codons that are generally rare in highly expressed genes of a given species by codons that are generally frequent in highly expressed genes of such species, such codons encoding the amino acids as the codons that are being exchanged.

A Method for Contracting a Repeat Sequence Subjected to Repeat Disorder

In another aspect, the present invention also relates to a method for contracting a repeat sequence within a genetic sequence subjected to repeat disorder into a living cell. This method comprises the steps of: (a) selecting a target sequence comprising a region adjacent to the repeat sequence; (b) providing at least one rare-cutting endonuclease capable of binding said target sequence and cleaving the repeat sequence; (c) introducing said rare-cutting endonuclease into said cell and (d) contacting said rare-cutting endonuclease with the genetic sequence such that said rare-cutting endonuclease cleaves the repeat sequence inducing a repair process conducting to the contraction of said repeat sequence. In a preferred embodiment said repair process is the single strand annealing (SSA). Single strand annealing (SSA) is a process that is initiated when a cleavage is made between two repeated sequences oriented in the same direction. Single stranded regions are created adjacent to the break that extend to the repeated sequences such that the complementary strands can anneal to each other. This annealed intermediate can be processed by digesting away the single stranded tails and filling in the gaps annealing process. In particular embodiment, the method comprises expressing within a cell the rare-cutting endonuclease capable of binding the target sequence according to the present invention. In a more particular embodiment, the method comprises transforming the cell with at least one polynucleotide encoding the rare-cutting endonuclease as described above and expressing said polynucleotide into said cell.

The method described above involves introducing rare-cutting endonuclease into a cell. As non-limiting example, said rare-cutting endouclease can be introduced as transgenes encoded by one plasmidic vector. Said plasmid vector can also contain a selection marker which provides for identification and/or selection of cells which received said vector.

Polypeptides may be synthesized in situ in the cell as a result of the introduction of polynucleotides encoding said polypeptides into the cell. Alternatively, said polypeptides could be produced outside the cell and then introduced thereto. Methods for introducing a polynucleotide construct into cells are known in the art and including as non limiting examples stable transformation methods wherein the polynucleotide construct is integrated into the genome of the cell, transient transformation methods wherein the polynucleotide construct is not integrated into the genome of the cell and virus mediated methods. Said polynucleotides may be introduced into a cell by for example, recombinant viral vectors (e.g. retroviruses, adenoviruses), liposome and the like. For example, transient transformation methods include for example microinjection, electroporation or particle bombardment. Said polynucleotides may be included in vectors, more particularly plasmids or virus, in view of being expressed in cells.

The present invention also relates to isolated cells or cell lines susceptible to be obtained by the method described in the above paragraph. In particular, said isolated cell comprises at least one rare-cutting endonuclease as described above. In another embodiment, said isolated cell comprises a reduced repeat expanded sequence. In a preferred embodiment, said isolated cell is a mammalian cell.

Applications

In another aspect, said rare-cutting endonuclease according to the present invention can be used to treat or prevent disease caused by the expansion of unstable repeats, preferably as non limiting examples: Fragile X syndrome (FRAXA), Fragile XE syndrome (FRAXE), Friedreich Ataxia (FRDA), Myotonic dystrophy (DM1), Fragile X-Associated Tremor Ataxia syndrome (FXTAS), CAG repeat expansion disease such as spinal and bulbar muscular atrophy (SBMA), Huntington disease (HD), spinocerebellar ataxia type 1, dentatorubal-pallidoluysian atrophy, Machado-Joseph disease, spinocerebellar ataxia 2, spinocerebellar ataxia 6 and spinocerebellar ataxia 7. Said rare cutting endonuclease of the present invention is preferably used to treat Huntington disease. Said rare-cutting endonuclease can be administrating directly to subjects (in vivo) using for example viral vector. Said rare-cutting endonuclease can be administrated by systemic administration (e.g. intravenous, intraperitoneal, intramuscular, subdermal or intracranial infusion) or topical application. Alternatively said rare-cutting endonuclease can be used to treat cells in vitro and then the modified cells are administrated to subjects, usually after selection for cells which have incorporated the vector (ex vivo).

The present invention also relates to a pharmaceutical composition comprising the rare-cutting endonuclease according to the present invention specific to a repeat sequence. The pharmaceutical composition according to the present invention can be used for contracting a specific repeat sequence within a cell. Pharmaceutically acceptable carriers are determined in part by the particular composition being administrated, as well as by the particular method used to administer the composition. Accordingly, there is a wide variety of suitable formulations of pharmaceutical compositions available.

The methods and compositions of the present invention are also useful for the design and implementation of in vitro and in vivo models, for example, animal models of repeat disorders, which allows for the study of these disorders. Non-limiting examples of suitable in vitro models include cells or cell lines from any organism, including fibroblast. Non limiting-examples of suitable animals for use as animal models include, invertebrates (*C. elegans, drsophilia*), rodents (e.g., rat or mouse), primate (e.g., non-human primates).

Definitions

In the description above, a number of terms are used extensively. The following definitions are provided to facilitate understanding of the present embodiments.

As used herein, "a" or "an" may mean one or more than one.

As used herein, the term "about" indicates that a value includes the inherent variation of error for the method being employed to determine a value, or the variation that exists among experiments.

Amino acid residues in a polypeptide sequence are designated herein according to the one-letter code, in which, for example, Q means Gln or Glutamine residue, R means Arg or Arginine residue and D means Asp or Aspartic acid residue.

Amino acid substitution means the replacement of one amino acid residue with another, for instance the replacement of an Arginine residue with a Glutamine residue in a peptide sequence is an amino acid substitution.

Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

As used herein, "nucleic acid" or "nucleic acid molecule" refers to nucleotides and/or polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Nucleic acids can be either single stranded or double stranded.

By "gene" is meant the basic unit of heredity, consisting of a segment of DNA arranged in a linear manner along a chromosome, which codes for a specific protein or segment of protein. A gene typically includes a promoter, a 5' untranslated region, one or more coding sequences (exons), optionally introns, a 3' untranslated region. The gene may further comprise a terminator, enhancers and/or silencers.

The term "cleavage" refers to the breakage of the covalent backbone of a polynucleotide. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. Double stranded DNA, RNA, or DNA/RNA hybrid cleavage can result in the production of either blunt ends or staggered ends.

By "catalytic domain" is intended the protein domain or module of an enzyme containing the active site of said enzyme; by active site is intended the part of said enzyme at which catalysis of the substrate occurs. Enzymes, but also their catalytic domains, are classified and named according to the reaction they catalyze. The Enzyme Commission number (EC number) is a numerical classification 10 scheme for enzymes, based on the chemical reactions they catalyze.

According to the invention, by "homologous" is meant, with respect to a first sequence of amino acids, any amino acid sequence having at least 60% or at least 70%, at least 80%, at least 85%, at least 90%, at least 95%, at least 98%, at least 99% homology with said first amino acid sequence, and having a similar biological activity.

Sequence homology can be identified by any method commonly used in the field by one skilled in the art. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting.

"identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting.

By "hybridization sequence" is meant the sequence part of the oligonucleotide that can hybridize to one of the other oligonucleotides under standard low stringent conditions. Such conditions can be for instance at room temperature for 2 hours by using a buffer containing 25% formamide, 4×SSC, 50 mM NaH2PO4/Na2HPO4 buffer; pH 7.0, 5×Denhardt's, 1 mM EDTA,1 mg/ml DNA +20 to 200 ng/ml probe to be tested (approx. 20-200 ng/ml)). This can be also predicted by standard calculation of hybridization using the number of complementary bases within the sequence and the content in G-C at room temperature as provided in the literature. Preferentially, the hybridization sequences are complementary to each other pursuant to the complementarity between two nucleic acid strands relying on Watson-Crick base pairing between the strands, i.e. the inherent base pairing between adenine and thymine (A-T) nucleotides and guanine and cytosine (G-C) nucleotides. Accurate base pairing equates with Watson-Crick base pairing includes base pairing between standard and modified nucleosides and base pairing between modified nucleosides, where the modified nucleosides are capable of substituting for the appropriate standard nucleosides according to the Watson-Crick pairing. The complementary sequence of the single-strand oligonucleotide can be any length that supports specific and stable hybridization between the two single-strand oligonucleotides under the reaction conditions.

By "delivery vector" or "delivery vectors" is intended any delivery vector which can be used in the present invention to put into cell contact (i.e "contacting") or deliver inside cells or subcellular compartments agents/chemicals and molecules (proteins or nucleic acids) needed in the present invention. It includes, but is not limited to liposomal delivery vectors, viral delivery vectors, drug delivery vectors, chemical carriers, polymeric carriers, lipoplexes, polyplexes, dendrimers, microbubbles (ultrasound contrast agents), nanoparticles, emulsions or other appropriate transfer vectors. These delivery vectors allow delivery of molecules, chemicals, macromolecules (genes, proteins), or other vectors such as plasmids, peptides developed by Diatos. In these cases, delivery vectors are molecule carriers. By "delivery vector" or "delivery vectors" is also intended delivery methods to perform transfection.

The terms "vector" or "vectors" refer to a nucleic acid molecule capable of transporting another nucleic acid to which it has been linked. A "vector" in the present invention includes, but is not limited to, a viral vector, a plasmid, a RNA vector or a linear or circular DNA or RNA molecule which may consists of a chromosomal, non chromosomal, semi-synthetic or synthetic nucleic acids.

Preferred vectors are those capable of autonomous replication (episomal vector) and/or expression of nucleic acids to which they are linked (expression vectors). Large numbers of suitable vectors are known to those of skill in the art and commercially available.

Viral vectors include retrovirus, adenovirus, parvovirus (e. g. adenoassociated viruses), coronavirus, negative strand RNA viruses such as orthomyxovirus (e. g., influenza virus), rhabdovirus (e. g., rabies and vesicular stomatitis virus), paramyxovirus (e. g. measles and Sendai), positive strand RNA viruses such as picornavirus and alphavirus, and double-stranded DNA viruses including adenovirus, herpesvirus (e. g., Herpes Simplex virus types 1 and 2, Epstein-Barr virus, cytomegalovirus), and poxvirus (e. g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

By cell or cells is intended any prokaryotic or eukaryotic living cells, cell lines derived from these organisms for in vitro cultures, primary cells from animal or plant origin.

By "primary cell" or "primary cells" are intended cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines. These cells thus represent a more valuable model to the in vivo state they refer to.

In the frame of the present invention, "eukaryotic cells" refer to a fungal, plant or animal cell or a cell line derived from the organisms listed below and established for in vitro culture.

More preferably the animal cell is of the genus *Homo, Rattus, Mus, Sus, Bos, Danio, Canis, Felis, Equus, Salmo, Oncorhynchus, Gallus, Meleagris, Drosophila, Caenorhabditis*; more preferably, the animal cell is of the species *Homo sapiens, Rattus norvegicus, Mus musculus, Sus scrofa, Bos taurus, Danio rerio, Canis lupus, Felis catus, Equus caballus, Salmo salar, Oncorhynchus mykiss, Gallus gallus, Meleagris gallopavo, Drosophila melanogaster, Caenorhabditis elegans.*

In the present invention, the cell can be a mammalian cell, a fish cell, an insect cell or cell lines derived from these organisms for in vitro cultures or primary cells taken directly from living tissue and established for in vitro culture. As non limiting examples cell lines can be selected from the group consisting of CHO-K1 cells; HEK293 cells; Caco2 cells; U2-OS cells; NIH 3T3 cells; NSO cells; SP2 cells; CHO-S cells; DG44 cells; K-562 cells, U-937 cells; MRC5 cells; IMR90 cells; Jurkat cells; HepG2 cells; HeLa cells; HT-1080 cells; HCT-116 cells; Hu-h7 cells; Huvec cells; Molt 4 cells. Are also encompassed in the scope of the present invention stem cells and induced Pluripotent Stem cells (iPS).

All these cell lines can be modified by the method of the present invention to provide cell line models.

The term "subject" as used herein includes all members of the animal kingdom including non-human primates and humans.

EXAMPLES

Cloning of the RVD Array Collection in the TALE Backbone

The two TALE backbones used in these experiment (pCLS9303 and pCLS9312, SEQ ID NO: 4 and 5) contain, between the C-terminal and the N-terminal domains, two BsmBI restriction sites. The individual repeat arrays targeting the region flanking the repeated trinucleotides (SEQ ID NO: 6 to 7) were subcloned in the pCLS9303 using type IIs restriction enzymes BsmBI for the receiving plasmid and BbvI and SfaNI for the inserted RVD array, leading to pCLS9984 and pCLS16715 (SEQ ID NO: 9 encoded SEQ ID NO: 8 and SEQ ID NO: 11 encoded SEQ ID NO: 10). The individual repeat arrays targeting the repeated trinulceotides (SEQ ID NO: 14) was subcloned in the pCLS9312 using type Is restriction enzymes BsmBI for the receiving plasmid and BbvI and SfaNI for the inserted RVD array, leading to pCLS9996 (SEQ ID NO: 16 encoded SEQ ID NO: 15). The monoclonality DNA sequence of each individual clone was assessed by DNA sequencing.

TALE-Nuclease Activities in Yeast

The two yeast target reporter plasmids containing the TALEN™ DNA target sequences were constructed as previously described (International PCT Applications WO 2004/067736 and in (Epinat, Arnould et al. 2003; Chames, Epinat et al. 2005; Arnould, Chames et al. 2006; Smith, Grizot et al. 2006). The TALEN™ pairs (pCLS9984/pCLS9996 and pCLS16715/pCLS9996) were tested at 37° C. and 30° C. in our yeast SSA assay previously described (International PCT Applications WO 2004/067736 and in (Epinat, Arnould et al. 2003; Chames, Epinat et al. 2005; Arnould, Chames et al. 2006; Smith, Grizot et al. 2006) on both targets (SEQ ID NO: 12 to 13, Table 1). TALEN™ cleavage activity levels on their targets in yeast are shown in Table 2.

TABLE 1

List of sequences targeted by the two TALEN pairs. The 16 bp sequence targeted by the TALEN ™ (position T0 is omitted) flanking the repeated sequence is underlined

| Name | Sequence |
|---|---|
| TiFLAN | TCTCAAGATTTCGCTGCAGCAGCAGCAGCAGCAGCAGCAGCAGCAGCAGCAGCAGCAGCAGCAGCAGCA |
| TiFLAN2_T01.1 | TGTGATCCCCCCAGCAGCAGCAGCAGCAGCAGCAGCAGCAGCAGCA |

TABLE 2

Activity of TALEN ™ in our yeast SSA assay previously described (International PCT Applications WO 2004/067736 and in (Epinat, Arnould et al. 2003; Chames, Epinat et al. 2005; Arnould, Chames et al. 2006; Smith, Grizot et al. 2006; Smith, Grizot et al. 2006) at 37° C. and 30° C.-represent no detectable activity, + indicate a weak activity and ++ represent a high activity. n.a. indicates no available data.

| At 37° C. | pCLS9984/ pCLS9996 | pCLS16715/ pCLS9996 |
|---|---|---|
| TiFLAN | +++ | - |
| TiFLAN2_T01.1 | + | +++ |
| At 30° C. | pCLS9984/ pCLS9996 | pCLS16715/ pCLS9996 |
| TiFLAN | +++ | - |
| TiFLAN2_T01.1 | - | ++ |

REFERENCES

Arnould, S., P. Chames, et al. (2006). "Engineering of large numbers of highly specific homing endonucleases that induce recombination on novel DNA targets." *J Mol Biol* 355(3): 443-58.

Atkins, J. F., N. M. Wills, et al. (2007). "A case for "StopGo": reprogramming translation to augment codon meaning of GGN by promoting unconventional termination (Stop) after addition of glycine and then allowing continued translation (Go)." *Rna* 13(6): 803-10.

Boch, J., H. Scholze, et al. (2009). "Breaking the code of DNA binding specificity of TAL-type III effectors." *Science* 326(5959): 1509-12.

Caplen, N. J., J. P. Taylor, et al. (2002). "Rescue of polyglutamine-mediated cytotoxicity by double-stranded RNA-mediated RNA interference." *Hum Mol Genet* 11(2): 175-84.

Chames, P., J. C. Epinat, et al. (2005). "In vivo selection of engineered homing endonucleases using double-strand break induced homologous recombination." *Nucleic Acids Res* 33(20): e178.

Christian, M., T. Cermak, et al. (2010). "Targeting DNA double-strand breaks with TAL effector nucleases." *Genetics* 186(2): 757-61.

Cong, L., F. A. Ran, et al. (2013). "Multiplex genome engineering using CRISPR/Cas systems." *Science* 339 (6121): 819-23.

DeJesus-Hernandez, M., I. R. Mackenzie, et al. (2011). "Expanded GGGGCC hexanucleotide repeat in noncoding region of C90RF72 causes chromosome 9p-linked FTD and ALS." *Neuron* 72(2): 245-56.

Deltcheva, E., K. Chylinski, et al. (2011). "CRISPR RNA maturation by trans-encoded small RNA and host factor RNase III." *Nature* 471(7340): 602-7.

DiFiglia, M., M. Sena-Esteves, et al. (2007). "Therapeutic silencing of mutant huntingtin with siRNA attenuates striatal and cortical neuropathology and behavioral deficits." *Proc Natl Acad Sci USA* 104(43): 17204-9.

Donnelly, M. and G. Elliott (2001). "Nuclear localization and shuttling of herpes simplex virus tegument protein VP13/14." *J Virol* 75(6): 2566-74.

Donnelly, M. L., G. Luke, et al. (2001). "Analysis of the aphthovirus 2A/2B polyprotein 'cleavage' mechanism indicates not a proteolytic reaction, but a novel translational effect: a putative ribosomal 'skip'." *J Gen Virol* 82(Pt 5): 1013-25.

Doronina, V. A., C. Wu, et al. (2008). "Site-specific release of nascent chains from ribosomes at a sense codon." *Mol Cell Biol* 28(13): 4227-39.

Dragatsis, I., M. S. Levine, et al. (2000). "Inactivation of Hdh in the brain and testis results in progressive neurodegeneration and sterility in mice." *Nat Genet* 26(3): 300-6.

Duyao, M. P., A. B. Auerbach, et al. (1995). "Inactivation of the mouse Huntington's disease gene homolog Hdh." *Science* 269(5222): 407-10.

Epinat, J. C., S. Arnould, et al. (2003). "A novel engineered meganuclease induces homologous recombination in yeast and mammalian cells." *Nucleic Acids Res* 31(11): 2952-62.

Garneau, J. E., M. E. Dupuis, et al. (2010). "The CRISPR/Cas bacterial immune system cleaves bacteriophage and plasmid DNA." *Nature* 468(7320): 67-71.

Garriga-Canut, M., C. Agustin-Pavon, et al. "Synthetic zinc finger repressors reduce mutant huntingtin expression in the brain of R6/2 mice." *Proc Natl Acad Sci USA* 109(45): E3136-45.

Gasiunas, G., R. Barrangou, et al. (2012). "Cas9-crRNA ribonucleoprotein complex mediates specific DNA cleavage for adaptive immunity in bacteria." *Proc Natl Acad Sci USA* 109(39): E2579-86.

Jinek, M., K. Chylinski, et al. (2012). "A programmable dual-RNA-guided DNA endonuclease in adaptive bacterial immunity." *Science* 337(6096): 816-21.

Lackner, G., N. Moebius, et al. (2011). "Complete genome sequence of *Burkholderia rhizoxinica*, an Endosymbiont of *Rhizopus microsporus." J Bacteriol* 193(3): 783-4.

Machida, Y., T. Okada, et al. (2006). "rAAV-mediated shRNA ameliorated neuropathology in Huntington disease model mouse." *Biochem Biophys Res Commun* 343 (1): 190-7.

Mali, P., L. Yang, et al. (2013). "RNA-guided human genome engineering via Cas9." *Science* 339(6121): 823-6.

Mirkin, S. M. (2007). "Expandable DNA repeats and human disease." *Nature* 447(7147): 932-40.

Moscou, M. J. and A. J. Bogdanove (2009). "A simple cipher governs DNA recognition by TAL effectors." *Science* 326(5959): 1501.

Nelson, D. L., H. T. Orr, et al. (2013). "The unstable repeats—three evolving faces of neurological disease." *Neuron* 77(5): 825-43.

Orr, H. T. and H. Y. Zoghbi (2007). "Trinucleotide repeat disorders." *Annu Rev Neurosci* 30: 575-621.

Renton, A. E., E. Majounie, et al. (2011). "A hexanucleotide repeat expansion in C9ORF72 is the cause of chromosome 9p21-linked ALS-FTD." *Neuron* 72(2): 257-68.

Richard, G. F., B. Dujon, et al. (1999). "Double-strand break repair can lead to high frequencies of deletions within short CAG/CTG trinucleotide repeats." *Mol Gen Genet* 261(4-5): 871-82.

Smith, J., S. Grizot, et al. (2006). "A combinatorial approach to create artificial homing endonucleases cleaving chosen sequences." *Nucleic Acids Res* 34(22): e149.

Smith, J., S. Grizot, et al. (2006). "A combinatorial approach to create artificial homing endonucleases cleaving chosen sequences." *Nucleic Acids Res.*

Sorek, R., C. M. Lawrence, et al. (2013). "CRISPR-mediated Adaptive Immune Systems in Bacteria and Archaea." *Annu Rev Biochem.*

Stoddard, B. L. (2005). "Homing endonuclease structure and function." *Q Rev Biophys* 38(1): 49-95.

Wang, Y. L., W. Liu, et al. (2005). "Clinico-pathological rescue of a model mouse of Huntington's disease by siRNA." *Neurosci Res* 53(3): 241-9.

The invention claimed is:

1. A method of contracting a repeat sequence within a genetic sequence in a cell, comprising:

(a) selecting a target sequence spanning the repeat sequence and a region adjacent to the repeat sequence;

(b) providing a rare-cutting endonuclease capable of binding said target sequence and cleaving the repeat sequence; and (c) introducing said rare-cutting endonuclease into said cell, wherein said rare-cutting endonuclease binds to the target sequence by recognizing at least 10 nucleic acid bases adjacent to the repeat sequence and at least 5 nucleic acid bases inside the repeat sequence;

such that the rare-cutting endonuclease induces cleavage within repeat sequence and induces contraction of the repeat sequence by Single Stranded Annealing, wherein the rare-cutting endonuclease has at least 80% amino acid sequence identity with a sequence selected from the group consisting of SEQ ID NO: 8, 10 and 15.

2. A method of contracting a repeat sequence within a genetic sequence in a cell, comprising:

(a) selecting a target sequence spanning the repeat sequence and a region adjacent to the repeat sequence;

(b) providing a rare-cutting endonuclease capable of binding said target sequence and cleaving the repeat sequence; and (c) introducing said rare-cutting endonuclease into said cell, wherein said rare-cutting endonuclease binds to the target sequence by recognizing at least 10 nucleic acid bases adjacent to the repeat sequence and at least 5 nucleic acid bases inside the repeat sequence;

such that the rare-cutting endonuclease induces cleavage within repeat sequence and induces contraction of the repeat sequence by Single Stranded Annealing, wherein the rare-cutting endonuclease has at least 85% amino acid sequence identity with a sequence selected from the group consisting of SEQ ID NO: 8, 10 and 15.

3. The method according to claim 1, wherein the rare-cutting endonuclease cuts within a poly-trinucleotide repeat of the HTT gene.

4. The method according to claim 2, wherein the rare-cutting endonuclease cuts within a poly-trinucleotide repeat of the HTT gene.

5. The method according to claim 1, wherein said target sequence is within a sequence selected from the group consisting of: SEQ ID NO: 1 to SEQ ID NO: 3.

6. The method according to claim 2, wherein said target sequence is within a sequence selected from the group consisting of: SEQ ID NO: 1 to SEQ ID NO: 3.

* * * * *

SEQUENCE LISTING

```
<160> NUMBER OF SEQ ID NOS: 16

<210> SEQ ID NO 1
<211> LENGTH: 13481
<212> TYPE: DNA
<213> ORGANISM: Homo sapiens
<220> FEATURE:
<223> OTHER INFORMATION: huntingtin (HTT) mRNA

<400> SEQUENCE: 1

gctgccggga cgggtccaag atggacggcc gctcaggttc tgcttttacc tgcggcccag      60

agccccattc attgccccgg tgctgagcgg cgccgcgagt cggcccgagg cctccgggga     120

ctgccgtgcc gggcgggaga ccgccatggc gaccctggaa aagctgatga aggccttcga     180

gtccctcaag tccttccagc agcagcagca gcagcagcag cagcagcagc agcagcagca     240

gcagcagcag cagcagcagc aacagccgcc accgccgccg ccgccgccgc cgcctcctca     300

gcttcctcag ccgccgccgc aggcacagcc gctgctgcct cagccgcagc cgcccccgcc     360

gccgcccccg ccgccacccg gcccggctgt ggctgaggag ccgctgcacc gaccaaagaa     420

agaactttca gctaccaaga aagaccgtgt gaatcattgt ctgacaatat gtgaaaacat     480

agtggcacag tctgtcagaa attctccaga atttcagaaa cttctgggca tcgctatgga     540

actttttctg ctgtgcagtg atgacgcaga gtcagatgtc aggatggtgg ctgacgaatg     600

cctcaacaaa gttatcaaag ctttgatgga ttctaatctt ccaaggttac agctcgagct     660

ctataaggaa attaaaaaga atggtgcccc tcggagtttg cgtgctgccc tgtggaggtt     720

tgctgagctg gctcacctgg ttcggcctca gaaatgcagg ccttacctgg tgaaccttct     780

gccgtgcctg actcgaacaa gcaagagacc cgaagaatca gtccaggaga ccttggctgc     840

agctgttccc aaaattatgg cttcttttgg caattttgca aatgacaatg aaattaaggt     900

tttgttaaag gccttcatag cgaacctgaa gtcaagctcc cccaccattc ggcggacagc     960

ggctggatca gcagtgagca tctgccagca ctcaagaagg acacaatatt tctatagttg    1020

gctactaaat gtgctcttag gcttactcgt tcctgtcgag gatgaacact ccactctgct    1080

gattcttggc gtgctgctca ccctgaggta tttggtgccc ttgctgcagc agcaggtcaa    1140

ggacacaagc ctgaaaggca gcttcggagt gacaaggaaa gaaatggaag tctctccttc    1200

tgcagagcag cttgtccagg tttatgaact gacgttacat catacacagc accaagacca    1260

caatgttgtg accggagccc tggagctgtt gcagcagctc ttcagaacgc ctccacccga    1320

gcttctgcaa accctgaccg cagtcggggg cattgggcag ctcaccgctg ctaaggagga    1380

gtctggtggc cgaagccgta gtgggagtat tgtggaactt atagctggag gggttcctc     1440
```

-continued

```
atgcagccct gtcctttcaa gaaaacaaaa aggcaaagtg ctcttaggag aagaagaagc   1500
cttggaggat gactctgaat cgagatcgga tgtcagcagc tctgccttaa cagcctcagt   1560
gaaggatgag atcagtggag agctggctgc ttcttcaggg gtttccactc cagggtcagc   1620
aggtcatgac atcatcacag aacagccacg gtcacagcac acactgcagg cggactcagt   1680
ggatctggcc agctgtgact tgacaagctc tgccactgat ggggatgagg aggatatctt   1740
gagccacagc tccagccagg tcagcgccgt cccatctgac cctgccatgg acctgaatga   1800
tgggacccag gcctcgtcgc ccatcagcga cagctcccag accaccaccg aagggcctga   1860
ttcagctgtt accccttcag acagttctga aattgtgtta gacggtaccg acaaccagta   1920
tttgggcctg cagattggac agccccagga tgaagatgag gaagccacag gtattcttcc   1980
tgatgaagcc tcggaggcct tcaggaactc ttccatggcc cttcaacagg cacatttatt   2040
gaaaaacatg agtcactgca ggcagccttc tgacagcagt gttgataaat ttgtgttgag   2100
agatgaagct actgaaccgg gtgatcaaga aaacaagcct tgccgcatca aaggtgacat   2160
tggacagtcc actgatgatg actctgcacc tcttgtccat tgtgtccgcc ttttatctgc   2220
ttcgtttttg ctaacagggg gaaaaaatgt gctggttccg gacagggatg tgagggtcag   2280
cgtgaaggcc ctggccctca gctgtgtggg agcagctgtg gccctccacc cggaatcttt   2340
cttcagcaaa ctctataaag ttcctcttga caccacggaa taccctgagg aacagtatgt   2400
ctcagacatc ttgaactaca tcgatcatgg agacccacag gttcgaggag ccactgccat   2460
tctctgtggg accctcatct gctccatcct cagcaggtcc cgcttccacg tgggagattg   2520
gatgggcacc attagaaccc tcacaggaaa tacattttct ttggcggatt gcattccttt   2580
gctgcggaaa acactgaagg atgagtcttc tgttacttgc aagttagctt gtacagctgt   2640
gaggaactgt gtcatgagtc tctgcagcag cagctacagt gagttaggac tgcagctgat   2700
catcgatgtg ctgactctga ggaacagttc ctattggctg gtgaggacag agcttctgga   2760
aacccttgca gagattgact tcaggctggt gagctttttg gaggcaaaag cagaaaactt   2820
acacagaggg gctcatcatt atacagggct tttaaaactg caagaacgag tgctcaataa   2880
tgttgtcatc catttgcttg gagatgaaga ccccagggtg cgacatgttg ccgcagcatc   2940
actaattagg cttgtcccaa agctgtttta taaatgtgac caaggacaag ctgatccagt   3000
agtggccgtg gcaagagatc aaagcagtgt ttacctgaaa cttctcatgc atgagacgca   3060
gcctccatct catttctccg tcagcacaat aaccagaata tatagaggct ataacctact   3120
accaagcata acagacgtca ctatggaaaa taacctttca agagttattg cagcagtttc   3180
tcatgaacta atcacatcaa ccaccagagc actcacattt ggatgctgtg aagctttgtg   3240
tcttctttcc actgccttcc cagtttgcat ttggagttta ggttggcact gtggagtgcc   3300
tccactgagt gcctcagatg agtctaggaa gagctgtacc gttgggatgg ccacaatgat   3360
tctgaccctg ctctcgtcag cttggttccc attggatctc tcagcccatc aagatgcttt   3420
gattttggcc ggaaacttgc ttgcagccag tgctcccaaa tctctgagaa gttcatgggc   3480
ctctgaagaa gaagccaacc cagcagccac caagcaagag gaggtctggc cagccctggg   3540
ggaccgggcc ctggtgccca tggtggagca gctcttctct cacctgctga aggtgattaa   3600
catttgtgcc cacgtcctgg atgacgtggc tcctggaccc gcaataaagg cagccttgcc   3660
ttctctaaca aaccccccctt ctctaagtcc catccgacga aaggggaagg agaaagaacc   3720
aggagaacaa gcatctgtac cgttgagtcc caagaaaggc agtgaggcca gtgcagcttc   3780
tagacaatct gatacctcag gtcctgttac aacaagtaaa tcctcatcac tggggagttt   3840
```

```
ctatcatctt ccttcatacc tcaaactgca tgatgtcctg aaagctacac acgctaacta   3900
caaggtcacg ctggatcttc agaacagcac ggaaaagttt ggagggtttc tccgctcagc   3960
cttggatgtt ctttctcaga tactagagct ggccacactg caggacattg ggaagtgtgt   4020
tgaagagatc ctaggatacc tgaaatcctg ctttagtcga gaaccaatga tggcaactgt   4080
ttgtgttcaa caattgttga agactctctt tggcacaaac ttggcctccc agtttgatgg   4140
cttatcttcc aaccccagca agtcacaagg ccgagcacag cgccttggct cctccagtgt   4200
gaggccaggc ttgtaccact actgcttcat ggccccgtac acccacttca cccaggccct   4260
cgctgacgcc agcctgagga acatggtgca ggcggagcag gagaacgaca cctcgggatg   4320
gtttgatgtc ctccagaaag tgtctaccca gttgaagaca aacctcacga gtgtcacaaa   4380
gaaccgtgca gataagaatg ctattcataa tcacattcgt ttgtttgaac ctcttgttat   4440
aaaagcttta aaacagtaca cgactacaac atgtgtgcag ttacagaagc aggttttaga   4500
tttgctggcg cagctggttc agttacgggt taattactgt cttctggatt cagatcaggt   4560
gtttattggc tttgtattga aacagtttga atacattgaa gtgggccagt tcagggaatc   4620
agaggcaatc attccaaaca tctttttctt cttggtatta ctatcttatg aacgctatca   4680
ttcaaaacag atcattggaa ttcctaaaat cattcagctc tgtgatggca tcatggccag   4740
tggaaggaag gctgtgacac atgccatacc ggctctgcag cccatagtcc acgacctctt   4800
tgtattaaga ggaacaaata aagctgatgc aggaaaagag cttgaaaccc aaaaagaggt   4860
ggtggtgtca atgttactga gactcatcca gtaccatcag gtgttggaga tgttcattct   4920
tgtcctgcag cagtgccaca aggagaatga agacaagtgg aagcgactgt ctcgacagat   4980
agctgacatc atcctcccaa tgttagccaa acagcagatg cacattgact ctcatgaagc   5040
ccttggagtg ttaaatacat tatttgagat tttggcccct tcctccctcc gtccggtaga   5100
catgctttta cggagtatgt tcgtcactcc aaacacaatg gcgtccgtga gcactgttca   5160
actgtggata tcgggaattc tggccatttt gagggttctg atttcccagt caactgaaga   5220
tattgttctt tctcgtattc aggagctctc cttctctccg tatttaatct cctgtacagt   5280
aattaatagg ttaagagatg gggacagtac ttcaacgcta gaagaacaca gtgaagggaa   5340
acaaataaag aatttgccag aagaaacatt ttcaaggttt ctattacaac tggttggtat   5400
tcttttagaa gacattgtta caaaacagct gaaggtggaa atgagtgagc agcaacatac   5460
tttctattgc caggaactag gcacactgct aatgtgtctg atccacatct tcaagtctgg   5520
aatgttccgg agaatcacag cagctgccac taggctgttc cgcagtgatg gctgtggcgg   5580
cagtttctac accctggaca gcttgaactt gcgggctcgt tccatgatca ccacccaccc   5640
ggccctggtg ctgctctggt gtcagatact gctgcttgtc aaccacaccg actaccgctg   5700
gtgggcagaa gtgcagcaga ccccgaaaag acacagtctg tccagcacaa agttacttag   5760
tccccagatg tctggagaag aggaggattc tgacttggca gccaaacttg gaatgtgcaa   5820
tagagaaata gtacgaagag gggctctcat tctcttctgt gattatgtct gtcagaacct   5880
ccatgactcc gagcacttaa cgtggctcat tgtaaatcac attcaagatc tgatcagcct   5940
ttcccacgag cctccagtac aggacttcat cagtgccgtt catcggaact ctgctgccag   6000
cggcctgttc atccaggcaa ttcagtctcg ttgtgaaaac ctttcaactc caaccatgct   6060
gaagaaaact cttcagtgct tggaggggat ccatctcagc cagtcgggag ctgtgctcac   6120
gctgtatgtg gacaggcttc tgtgcacccc tttccgtgtg ctggctcgca tggtcgacat   6180
```

```
ccttgcttgt cgccgggtag aaatgcttct ggctgcaaat ttacagagca gcatggccca   6240
gttgccaatg gaagaactca acagaatcca ggaatacctt cagagcagcg ggctcgctca   6300
gagacaccaa aggctctatt ccctgctgga caggtttcgt ctctccacca tgcaagactc   6360
acttagtccc tctcctccag tctcttccca cccgctggac ggggatgggc acgtgtcact   6420
ggaaacagtg agtccggaca aagactggta cgttcatctt gtcaaatccc agtgttggac   6480
caggtcagat tctgcactgc tggaaggtgc agagctggtg aatcggattc ctgctgaaga   6540
tatgaatgcc ttcatgatga actcggagtt caacctaagc ctgctagctc catgcttaag   6600
cctagggatg agtgaaattt ctggtggcca gaagagtgcc ctttttgaag cagcccgtga   6660
ggtgactctg gcccgtgtga gcggcaccgt gcagcagctc cctgctgtcc atcatgtctt   6720
ccagcccgag ctgcctgcag agccggcggc ctactggagc aagttgaatg atctgtttgg   6780
ggatgctgca ctgtatcagt ccctgcccac tctggcccgg gccctggcac agtacctggt   6840
ggtggtctcc aaactgccca gtcatttgca ccttcctcct gagaaagaga aggacattgt   6900
gaaattcgtg gtggcaaccc ttgaggccct gtcctggcat ttgatccatg agcagatccc   6960
gctgagtctg gatctccagg cagggctgga ctgctgctgc ctggccctgc agctgcctgg   7020
cctctggagc gtggtctcct ccacagagtt tgtgacccac gcctgctccc tcatctactg   7080
tgtgcacttc atcctggagg ccgttgcagt gcagcctgga gagcagcttc ttagtccaga   7140
aagaaggaca aataccccaa aagccatcag cgaggaggag gaggaagtag atccaaacac   7200
acagaatcct aagtatatca ctgcagcctg tgagatggtg gcagaaatgg tggagtctct   7260
gcagtcggtg ttggccttgg gtcataaaag gaatagcggc gtgccggcgt ttctcacgcc   7320
attgctaagg aacatcatca tcagcctggc ccgcctgccc cttgtcaaca gctacacacg   7380
tgtgccccca ctggtgtgga agcttggatg gtcacccaaa ccgggagggg attttggcac   7440
agcattccct gagatccccg tggagttcct ccaggaaaag gaagtcttta aggagttcat   7500
ctaccgcatc aacacactag gctggaccag tcgtactcag tttgaagaaa cttgggccac   7560
cctccttggt gtcctggtga cgcagcccct cgtgatggag caggaggaga gcccaccaga   7620
agaagacaca gagaggaccc agatcaacgt cctggccgtg caggccatca cctcactggt   7680
gctcagtgca atgactgtgc ctgtggccgg caacccagct gtaagctgct tggagcagca   7740
gccccggaac aagcctctga aagctctcga caccaggttt gggaggaagc tgagcattat   7800
cagagggatt gtggagcaag agattcaagc aatggtttca aagagagaga atattgccac   7860
ccatcattta tatcaggcat gggatcctgt cccttctctg tctccggcta ctacaggtgc   7920
cctcatcagc cacgagaagc tgctgctaca gatcaacccc gagcgggagc tggggagcat   7980
gagctacaaa ctcggccagg tgtccataca ctccgtgtgg ctggggaaca gcatcacacc   8040
cctgagggag gaggaatggg acgaggaaga ggaggaggag gccgacgccc ctgcaccttc   8100
gtcaccaccc acgtctccag tcaactccag gaaacaccgg gctggagttg acatccactc   8160
ctgttcgcag tttttgcttg agttgtacag ccgctggatc ctgccgtcca gctcagccag   8220
gaggaccccg gccatcctga tcagtgaggt ggtcagatcc cttctagtgg tctcagactt   8280
gttcaccgag cgcaaccagt ttgagctgat gtatgtgacg ctgacagaac tgcgaagggt   8340
gcacccttca gaagacgaga tcctcgctca gtacctggtg cctgccacct gcaaggcagc   8400
tgccgtcctt gggatggaca aggccgtggc ggagcctgtc agccgcctgc tggagagcac   8460
gctcaggagc agccacctgc ccagcagggt tggagccctg cacggcgtcc tctatgtgct   8520
ggagtgcgac ctgctggacg acactgccaa gcagctcatc ccggtcatca gcgactatct   8580
```

```
cctctccaac ctgaaaggga tcgcccactg cgtgaacatt cacagccagc agcacgtact   8640
ggtcatgtgt gccactgcgt tttacctcat tgagaactat cctctggacg tagggccgga   8700
attttcagca tcaataatac agatgtgtgg ggtgatgctg tctggaagtg aggagtccac   8760
cccctccatc atttaccact gtgccctcag aggcctggag cgcctcctgc tctctgagca   8820
gctctcccgc ctggatgcag aatcgctggt caagctgagt gtggacagag tgaacgtgca   8880
cagcccgcac cgggccatgg cggctctggg cctgatgctc acctgcatgt acacaggaaa   8940
ggagaaagtc agtccgggta gaacttcaga ccctaatcct gcagcccccg acagcgagtc   9000
agtgattgtt gctatggagc gggtatctgt tctttttgat aggatcagga aaggctttcc   9060
ttgtgaagcc agagtggtgg ccaggatcct gccccagttt ctagacgact tcttcccacc   9120
ccaggacatc atgaacaaag tcatcggaga gtttctgtcc aaccagcagc catacccccca  9180
gttcatggcc accgtggtgt ataaggtgtt tcagactctg cacagcaccg ggcagtcgtc   9240
catggtccgg gactgggtca tgctgtccct ctccaacttc acgcagaggg ccccggtcgc   9300
catggccacg tggagcctct cctgcttctt tgtcagcgcg tccaccagcc cgtgggtcgc   9360
ggcgatcctc ccacatgtca tcagcaggat gggcaagctg gagcaggtgg acgtgaacct   9420
tttctgcctg gtcgccacag acttctacag acaccagata gaggaggagc tcgaccgcag   9480
ggccttccag tctgtgcttg aggtggttgc agccccagga agcccatatc accggctgct   9540
gacttgttta cgaaatgtcc acaaggtcac cacctgctga gcgccatggt gggagagact   9600
gtgaggcggc agctggggcc ggagcctttg gaagtctgcg cccttgtgcc ctgcctccac   9660
cgagccagct tggtccctat gggcttccgc acatgccgcg ggcggccagg caacgtgcgt   9720
gtctctgcca tgtggcagaa gtgctctttg tggcagtggc caggcaggga gtgtctgcag   9780
tcctggtggg gctgagcctg aggccttcca gaaagcagga gcagctgtgc tgcaccccat   9840
gtgggtgacc aggtcctttc tcctgatagt cacctgctgg ttgttgccag gttgcagctg   9900
ctcttgcatc tgggccagaa gtcctccctc ctgcaggctg gctgttggcc cctctgctgt   9960
cctgcagtag aaggtgccgt gagcaggctt tgggaacact ggcctgggtc tccctggtgg   10020
ggtgtgcatg ccacgccccg tgtctggatg cacagatgcc atggcctgtg ctgggccagt   10080
ggctgggggt gctagacacc cggcaccatt ctcccttctc tcttttcttc tcaggattta   10140
aaatttaatt atatcagtaa agagattaat tttaacgtaa ctctttctat gcccgtgtaa   10200
agtatgtgaa tcgcaaggcc tgtgctgcat gcgacagcgt ccggggtggt ggacagggcc   10260
cccggccacg ctccctctcc tgtagccact ggcatagccc tcctgagcac ccgctgacat   10320
ttccgttgta catgttcctg tttatgcatt cacaaggtga ctgggatgta gagaggcgtt   10380
agtgggcagg tggccacagc aggactgagg acaggccccc attatcctag gggtgcgctc   10440
acctgcagcc cctcctcctc gggcacagac gactgtcgtt ctccacccac cagtcaggga   10500
cagcagcctc cctgtcactc agctgagaag gccagccctc cctggctgtg agcagcctcc   10560
actgtgtcca gagacatggg cctcccactc ctgttccttg ctagccctgg ggtggcgtct   10620
gcctaggagc tggctggcag gtgttgggac ctgctgctcc atggatgcat gccctaagag   10680
tgtcactgag ctgtgttttg tctgagcctc tctcggtcaa cagcaaagct tggtgtcttg   10740
gcactgttag tgacagagcc cagcatccct tctgccccccg ttccagctga catcttgcac  10800
ggtgacccct tttagtcagg agagtgcaga tctgtgctca tcggagactg ccccacggcc   10860
ctgtcagagc cgccactcct atccccaggc caggtccctg gaccagcctc ctgtttgcag   10920
```

```
gcccagagga gccaagtcat taaaatggaa gtggattctg gatggccggg ctgctgctga  10980
tgtaggagct ggatttggga gctctgcttg ccgactggct gtgagacgag gcaggggctc  11040
tgcttcctca gccctagagg cgagccaggc aaggttggcg actgtcatgt ggcttggttt  11100
ggtcatgccc gtcgatgttt tgggtattga atgtggtaag tggaggaaat gttggaactc  11160
tgtgcaggtg ctgccttgag acccccaagc ttccacctgt ccctctccta tgtggcagct  11220
ggggagcagc tgagatgtgg acttgtatgc tgcccacata cgtgaggggg agctgaaagg  11280
gagcccctcc tctgagcagc ctctgccagg cctgtatgag gcttttccca ccagctccca  11340
acagaggcct cccccagcca ggaccacctc gtcctcgtgg cggggcagca ggagcggtag  11400
aaaggggtcc gatgtttgag gaggccctta agggaagcta ctgaattata acacgtaaga  11460
aaatcaccat tccgtattgg ttgggggctc ctgtttctca tcctagcttt ttcctggaaa  11520
gcccgctaga aggtttggga acgaggggaa agttctcaga actgttggct gctccccacc  11580
cgcctcccgc ctcccccgca ggttatgtca gcagctctga gacagcagta tcacaggcca  11640
gatgttgttc ctggctagat gtttacattt gtaagaaata acactgtgaa tgtaaaacag  11700
agccattccc ttggaatgca tatcgctggg ctcaacatag agtttgtctt cctcttgttt  11760
acgacgtgat ctaaaccagt ccttagcaag ggctcagaa caccccgctc tggcagtagg  11820
tgtcccccac ccccaaagac ctgcctgtgt gctccggaga tgaatatgag ctcattagta  11880
aaaatgactt cacccacgca tatacataaa gtatccatgc atgtgcatat agacacatct  11940
ataattttac acacacacct ctcaagacgg agatgcatgg cctctaagag tgcccgtgtc  12000
ggttcttcct ggaagttgac tttccttaga cccgccaggt caagttagcc gcgtgacgga  12060
catccaggcg tgggacgtgg tcagggcagg gctcattcat tgcccactag gatcccactg  12120
gcgaagatgg tctccatatc agctctctgc agaagggagg aagactttat catgttccta  12180
aaaatctgtg gcaagcaccc atcgtattat ccaaattttg ttgcaaatgt gattaatttg  12240
gttgtcaagt tttgggggtg ggctgtgggg agattgcttt tgttttcctg ctggtaatat  12300
cgggaaagat tttaatgaaa ccagggtaga attgtttggc aatgcactga agcgtgtttc  12360
tttcccaaaa tgtgcctccc ttccgctgcg ggcccagctg agtctatgta ggtgatgttt  12420
ccagctgcca agtgctcttt gttactgtcc accctcattt ctgccagcgc atgtgtcctt  12480
tcaaggggaa aatgtgaagc tgaacccccct ccagacaccc agaatgtagc atctgagaag  12540
gccctgtgcc ctaaaggaca cccctcgccc ccatcttcat ggagggggtc atttcagagc  12600
cctcggagcc aatgaacagc tcctcctctt ggagctgaga tgagccccac gtggagctcg  12660
ggacggatag tagacagcaa taactcggtg tgtggccgcc tggcaggtgg aacttcctcc  12720
cgttgcgggg tggagtgagg ttagttctgt gtgtctggtg ggtggagtca ggcttctctt  12780
gctacctgtg agcatccttc ccagcagaca tcctcatcgg gctttgtccc tcccccgctt  12840
cctccctctg cggggaggac ccgggaccac agctgctggc cagggtagac ttggagctgt  12900
cctccagagg ggtcacgtgt aggagtgaga agaaggaaga tcttgagagc tgctgaggga  12960
ccttggagag ctcaggatgg ctcagacgag gacactcgct tgccgggcct gggcctcctg  13020
ggaaggaggg agctgctcag aatgccgcat gacaactgaa ggcaacctgg aaggttcagg  13080
ggccgctctt cccccatgtg cctgtcacgc tctggtgcag tcaaaggaac gccttcccct  13140
cagttgtttc taagagcaga gtctcccgct gcaatctggg tggtaactgc cagccttgga  13200
ggatcgtggc caacgtggac ctgcctacgg agggtgggct ctgacccaag tggggcctcc  13260
ttgtccaggt ctcactgctt tgcaccgtgg tcagagggac tgtcagctga gcttgagctc  13320
```

```
ccctggagcc agcagggctg tgatgggcga gtcccggagc cccacccaga cctgaatgct  13380

tctgagagca aagggaagga ctgacgagag atgtatattt aattttttaa ctgctgcaaa  13440

cattgtacat ccaaattaaa ggaaaaaaat ggaaaccatc a                      13481


<210> SEQ ID NO 2
<211> LENGTH: 259
<212> TYPE: DNA
<213> ORGANISM: Homo sapiens
<220> FEATURE:
<223> OTHER INFORMATION: fragment of huntingtin (HTT) mRNA (residues 1
      to 259)

<400> SEQUENCE: 2

gctgccggga cgggtccaag atggacggcc gctcaggttc tgcttttacc tgcggcccag     60

agccccattc attgccccgg tgctgagcgg cgccgcgagt cggcccgagg cctccgggga    120

ctgccgtgcc gggcgggaga ccgccatggc gaccctggaa aagctgatga aggccttcga    180

gtccctcaag tccttccagc agcagcagca gcagcagcag cagcagcagc agcagcagca    240

gcagcagcag cagcagcag                                                 259


<210> SEQ ID NO 3
<211> LENGTH: 31
<212> TYPE: DNA
<213> ORGANISM: Homo sapiens
<220> FEATURE:
<223> OTHER INFORMATION: fragment of huntingtin (HTT) mRNA (residues 181
      to 211)

<400> SEQUENCE: 3

gtccctcaag tccttccagc agcagcagca g                                    31


<210> SEQ ID NO 4
<211> LENGTH: 1266
<212> TYPE: DNA
<213> ORGANISM: Artificial sequence
<220> FEATURE:
<223> OTHER INFORMATION: Description of artificial sequence: Synthetic
      polynucleotide
<220> FEATURE:
<223> OTHER INFORMATION: pCLS9303

<400> SEQUENCE: 4

atgggcgatc ctaaaaagaa acgtaaggtc atcgattacc catacgatgt tccagattac     60

gctatcgata tcgccgatct acgcacgctc ggctacagcc agcagcaaca ggagaagatc    120

aaaccgaagg ttcgttcgac agtggcgcag caccacgagg cactggtcgg ccacgggttt    180

acacacgcgc acatcgttgc gttaagccaa cacccggcag cgttagggac cgtcgctgtc    240

aagtatcagg acatgatcgc agcgttgcca gaggcgacac acgaagcgat cgttggcgtc    300

ggcaaacagt ggtccggcgc acgcgctctg gaggccttgc tcacggtggc gggagagttg    360

agaggtccac cgttacagtt ggacacaggc caacttctca agattgcaaa acgtggcggc    420

gtgaccgcag tggaggcagt gcatgcatgg cgcaatgcac tgacgggtgc cccgctcaac    480

ttgaccggag acgcccgggg gatcaggtca cgtgcgtctc ggagcattgt tgcccagtta    540

tctcgccctg atccggcgtt ggccgcgttg accaacgacc acctcgtcgc cttggcctgc    600

ctcggcgggc gtcctgcgct ggatgcagtg aaaaagggat tgggggatcc tatcagccgt    660

tcccagctgg tgaagtccga gctggaggag aagaaatccg agttgaggca caagctgaag    720

tacgtgcccc acgagtacat cgagctgatc gagatcgccc ggaacagcac ccaggaccgt    780
```

```
atcctggaga tgaaggtgat ggagttcttc atgaaggtgt acggctacag gggcaagcac    840

ctgggcggct ccaggaagcc cgacggcgcc atctacaccg tgggctcccc catcgactac    900

ggcgtgatcg tggacaccaa ggcctactcc ggcggctaca acctgcccat cggccaggcc    960

gacgaaatgc agaggtacgt ggaggagaac cagaccagga acaagcacat caaccccaac   1020

gagtggtgga aggtgtaccc ctccagcgtg accgagttca agttcctgtt cgtgtccggc   1080

cacttcaagg gcaactacaa ggcccagctg accaggctga accacatcac caactgcaac   1140

ggcgccgtgc tgtccgtgga ggagctcctg atcggcggcg agatgatcaa ggccggcacc   1200

ctgaccctgg aggaggtgag gaggaagttc aacaacggcg agatcaactt cgcggccgac   1260

tgataa                                                              1266
```

<210> SEQ ID NO 5
<211> LENGTH: 1284
<212> TYPE: DNA
<213> ORGANISM: Artificial sequence
<220> FEATURE:
<223> OTHER INFORMATION: Description of artificial sequence: Synthetic polynucleotide
<220> FEATURE:
<223> OTHER INFORMATION: pCLS9312

<400> SEQUENCE: 5

```
atgggcgatc ctaaaaagaa acgtaaggtc atcgataagg agaccgccgc tgccaagttc     60

gagagacagc acatggacag catcgatatc gccgatctac gcacgctcgg ctacagccag    120

cagcaacagg agaagatcaa accgaaggtt cgttcgacag tggcgcagca ccacgaggca    180

ctggtcggcc acgggtttac acacgcgcac atcgttgcgt taagccaaca cccggcagcg    240

ttagggaccg tcgctgtcaa gtatcaggac atgatcgcag cgttgccaga ggcgacacac    300

gaagcgatcg ttggcgtcgg caaacagtgg tccggcgcac gcgctctgga ggccttgctc    360

acggtggcgg gagagttgag aggtccaccg ttacagttgg acacaggcca acttctcaag    420

attgcaaaac gtggcggcgt gaccgcagtg gaggcagtgc atgcatggcg caatgcactg    480

acgggtgccc cgctcaactt gaccggagac gcccggggga tcaggtcacg tgcgtctcgg    540

agcattgttg cccagttatc tcgccctgat ccggcgttgg ccgcgttgac caacgaccac    600

ctcgtcgcct tggcctgcct cggcgggcgt cctgcgctgg atgcagtgaa aaagggattg    660

ggggatccta tcagccgttc ccagctggtg aagtccgagc tggaggagaa gaaatccgag    720

ttgaggcaca agctgaagta cgtgccccac gagtacatcg agctgatcga gatcgcccgg    780

aacagcaccc aggaccgtat cctggagatg aaggtgatgg agttcttcat gaaggtgtac    840

ggctacaggg gcaagcacct gggcggctcc aggaagcccg acggcgccat ctacaccgtg    900

ggctccccca tcgactacgg cgtgatcgtg gacaccaagg cctactccgg cggctacaac    960

ctgcccatcg gccaggccga cgaaatgcag aggtacgtgg aggagaacca gaccaggaac   1020

aagcacatca accccaacga gtggtggaag gtgtacccct ccagcgtgac cgagttcaag   1080

ttcctgttcg tgtccggcca cttcaagggc aactacaagg cccagctgac caggctgaac   1140

cacatcacca actgcaacgg cgccgtgctg tccgtggagg agctcctgat cggcggcgag   1200

atgatcaagg ccggcaccct gaccctggag gaggtgagga ggaagttcaa caacggcgag   1260

atcaacttcg cggccgactg ataa                                          1284
```

<210> SEQ ID NO 6
<211> LENGTH: 530

```
<212> TYPE: PRT
<213> ORGANISM: Artificial sequence
<220> FEATURE:
<223> OTHER INFORMATION: Description of artificial sequence: Synthetic
      polypeptide
<220> FEATURE:
<223> OTHER INFORMATION: TiFLAN

<400> SEQUENCE: 6

Leu Thr Pro Gln Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Asn Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Gln Gln Val Val Ala
    130                 135                 140

Ile Ala Ser Asn Gly Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Asn Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser His Asp Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
            260                 265                 270

Leu Thr Pro Gln Gln Val Val Ala Ile Ala Ser Asn Asn Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
            340                 345                 350

Ile Gly Gly Lys Gln Ala Leu Glu Thr Val Gln Ala Leu Leu Pro Val
        355                 360                 365
```

```
Leu Cys Gln Ala His Gly Leu Thr Pro Gln Gln Val Val Ala Ile Ala
    370                 375                 380

Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser His Asp Gly Gly Lys Gln Ala Leu Glu Thr Val Gln Arg
            420                 425                 430

Leu Leu Pro Val Leu Cys Gln Ala His Gly Leu Thr Pro Glu Gln Val
        435                 440                 445

Val Ala Ile Ala Ser Asn Ile Gly Gly Lys Gln Ala Leu Glu Thr Val
    450                 455                 460

Gln Ala Leu Leu Pro Val Leu Cys Gln Ala His Gly Leu Thr Pro Gln
465                 470                 475                 480

Gln Val Val Ala Ile Ala Ser Asn Asn Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530


<210> SEQ ID NO 7
<211> LENGTH: 530
<212> TYPE: PRT
<213> ORGANISM: Artificial sequence
<220> FEATURE:
<223> OTHER INFORMATION: Description of artificial sequence: Synthetic
      polypeptide
<220> FEATURE:
<223> OTHER INFORMATION: TiFLAN2_T01.1

<400> SEQUENCE: 7

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Gly Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Asn Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser Asn Ile Gly Gly Lys Gln Ala Leu Glu Thr Val Gln Ala Leu Leu
        115                 120                 125

Pro Val Leu Cys Gln Ala His Gly Leu Thr Pro Gln Gln Val Val Ala
    130                 135                 140

Ile Ala Ser Asn Gly Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175
```

```
Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser His Asp Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser His Asp Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser His
            340                 345                 350

Asp Gly Gly Lys Gln Ala Leu Glu Thr Val Gln Arg Leu Leu Pro Val
        355                 360                 365

Leu Cys Gln Ala His Gly Leu Thr Pro Glu Gln Val Val Ala Ile Ala
    370                 375                 380

Ser Asn Ile Gly Gly Lys Gln Ala Leu Glu Thr Val Gln Ala Leu Leu
385                 390                 395                 400

Pro Val Leu Cys Gln Ala His Gly Leu Thr Pro Gln Gln Val Val Ala
                405                 410                 415

Ile Ala Ser Asn Asn Gly Gly Lys Gln Ala Leu Glu Thr Val Gln Arg
            420                 425                 430

Leu Leu Pro Val Leu Cys Gln Ala His Gly Leu Thr Pro Glu Gln Val
        435                 440                 445

Val Ala Ile Ala Ser His Asp Gly Gly Lys Gln Ala Leu Glu Thr Val
    450                 455                 460

Gln Arg Leu Leu Pro Val Leu Cys Gln Ala His Gly Leu Thr Pro Glu
465                 470                 475                 480

Gln Val Val Ala Ile Ala Ser Asn Ile Gly Gly Lys Gln Ala Leu Glu
                485                 490                 495

Thr Val Gln Ala Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530


<210> SEQ ID NO 8
<211> LENGTH: 936
<212> TYPE: PRT
<213> ORGANISM: Artificial sequence
<220> FEATURE:
<223> OTHER INFORMATION: Description of artificial sequence: Synthetic
      polypeptide
<220> FEATURE:
<223> OTHER INFORMATION: pCLS9984
```

<400> SEQUENCE: 8

```
Met Gly Asp Pro Lys Lys Lys Arg Lys Val Ile Asp Tyr Pro Tyr Asp
1               5                   10                  15

Val Pro Asp Tyr Ala Ile Asp Ile Ala Asp Leu Arg Thr Leu Gly Tyr
            20                  25                  30

Ser Gln Gln Gln Gln Glu Lys Ile Lys Pro Lys Val Arg Ser Thr Val
        35                  40                  45

Ala Gln His His Glu Ala Leu Val Gly His Gly Phe Thr His Ala His
    50                  55                  60

Ile Val Ala Leu Ser Gln His Pro Ala Ala Leu Gly Thr Val Ala Val
65                  70                  75                  80

Lys Tyr Gln Asp Met Ile Ala Ala Leu Pro Glu Ala Thr His Glu Ala
                85                  90                  95

Ile Val Gly Val Gly Lys Gln Trp Ser Gly Ala Arg Ala Leu Glu Ala
            100                 105                 110

Leu Leu Thr Val Ala Gly Glu Leu Arg Gly Pro Pro Leu Gln Leu Asp
        115                 120                 125

Thr Gly Gln Leu Leu Lys Ile Ala Lys Arg Gly Gly Val Thr Ala Val
    130                 135                 140

Glu Ala Val His Ala Trp Arg Asn Ala Leu Thr Gly Ala Pro Leu Asn
145                 150                 155                 160

Leu Thr Pro Gln Gln Val Val Ala Ile Ala Ser Asn Gly Gly Gly Lys
                165                 170                 175

Gln Ala Leu Glu Thr Val Gln Arg Leu Leu Pro Val Leu Cys Gln Ala
            180                 185                 190

His Gly Leu Thr Pro Glu Gln Val Val Ala Ile Ala Ser His Asp Gly
        195                 200                 205

Gly Lys Gln Ala Leu Glu Thr Val Gln Arg Leu Leu Pro Val Leu Cys
    210                 215                 220

Gln Ala His Gly Leu Thr Pro Gln Gln Val Val Ala Ile Ala Ser Asn
225                 230                 235                 240

Asn Gly Gly Lys Gln Ala Leu Glu Thr Val Gln Arg Leu Leu Pro Val
                245                 250                 255

Leu Cys Gln Ala His Gly Leu Thr Pro Glu Gln Val Val Ala Ile Ala
            260                 265                 270

Ser His Asp Gly Gly Lys Gln Ala Leu Glu Thr Val Gln Arg Leu Leu
        275                 280                 285

Pro Val Leu Cys Gln Ala His Gly Leu Thr Pro Gln Gln Val Val Ala
    290                 295                 300

Ile Ala Ser Asn Gly Gly Gly Lys Gln Ala Leu Glu Thr Val Gln Arg
305                 310                 315                 320

Leu Leu Pro Val Leu Cys Gln Ala His Gly Leu Thr Pro Gln Gln Val
                325                 330                 335

Val Ala Ile Ala Ser Asn Asn Gly Gly Lys Gln Ala Leu Glu Thr Val
            340                 345                 350

Gln Arg Leu Leu Pro Val Leu Cys Gln Ala His Gly Leu Thr Pro Glu
        355                 360                 365

Gln Val Val Ala Ile Ala Ser His Asp Gly Gly Lys Gln Ala Leu Glu
    370                 375                 380

Thr Val Gln Arg Leu Leu Pro Val Leu Cys Gln Ala His Gly Leu Thr
385                 390                 395                 400

Pro Glu Gln Val Val Ala Ile Ala Ser Asn Ile Gly Gly Lys Gln Ala
```

-continued

```
                405                 410                 415

Leu Glu Thr Val Gln Ala Leu Leu Pro Val Leu Cys Gln Ala His Gly
            420                 425                 430

Leu Thr Pro Gln Gln Val Val Ala Ile Ala Ser Asn Asn Gly Gly Lys
        435                 440                 445

Gln Ala Leu Glu Thr Val Gln Arg Leu Leu Pro Val Leu Cys Gln Ala
    450                 455                 460

His Gly Leu Thr Pro Glu Gln Val Val Ala Ile Ala Ser His Asp Gly
465                 470                 475                 480

Gly Lys Gln Ala Leu Glu Thr Val Gln Arg Leu Leu Pro Val Leu Cys
                485                 490                 495

Gln Ala His Gly Leu Thr Pro Glu Gln Val Val Ala Ile Ala Ser Asn
            500                 505                 510

Ile Gly Gly Lys Gln Ala Leu Glu Thr Val Gln Ala Leu Leu Pro Val
        515                 520                 525

Leu Cys Gln Ala His Gly Leu Thr Pro Gln Gln Val Val Ala Ile Ala
    530                 535                 540

Ser Asn Asn Gly Gly Lys Gln Ala Leu Glu Thr Val Gln Arg Leu Leu
545                 550                 555                 560

Pro Val Leu Cys Gln Ala His Gly Leu Thr Pro Glu Gln Val Val Ala
                565                 570                 575

Ile Ala Ser His Asp Gly Gly Lys Gln Ala Leu Glu Thr Val Gln Arg
            580                 585                 590

Leu Leu Pro Val Leu Cys Gln Ala His Gly Leu Thr Pro Glu Gln Val
        595                 600                 605

Val Ala Ile Ala Ser Asn Ile Gly Gly Lys Gln Ala Leu Glu Thr Val
    610                 615                 620

Gln Ala Leu Leu Pro Val Leu Cys Gln Ala His Gly Leu Thr Pro Gln
625                 630                 635                 640

Gln Val Val Ala Ile Ala Ser Asn Asn Gly Gly Lys Gln Ala Leu Glu
                645                 650                 655

Thr Val Gln Arg Leu Leu Pro Val Leu Cys Gln Ala His Gly Leu Thr
            660                 665                 670

Pro Gln Gln Val Val Ala Ile Ala Ser Asn Gly Gly Gly Arg Pro Ala
        675                 680                 685

Leu Glu Ser Ile Val Ala Gln Leu Ser Arg Pro Asp Pro Ala Leu Ala
    690                 695                 700

Ala Leu Thr Asn Asp His Leu Val Ala Leu Ala Cys Leu Gly Gly Arg
705                 710                 715                 720

Pro Ala Leu Asp Ala Val Lys Lys Gly Leu Gly Asp Pro Ile Ser Arg
                725                 730                 735

Ser Gln Leu Val Lys Ser Glu Leu Glu Glu Lys Lys Ser Glu Leu Arg
            740                 745                 750

His Lys Leu Lys Tyr Val Pro His Glu Tyr Ile Glu Leu Ile Glu Ile
        755                 760                 765

Ala Arg Asn Ser Thr Gln Asp Arg Ile Leu Glu Met Lys Val Met Glu
    770                 775                 780

Phe Phe Met Lys Val Tyr Gly Tyr Arg Gly Lys His Leu Gly Gly Ser
785                 790                 795                 800

Arg Lys Pro Asp Gly Ala Ile Tyr Thr Val Gly Ser Pro Ile Asp Tyr
                805                 810                 815

Gly Val Ile Val Asp Thr Lys Ala Tyr Ser Gly Gly Tyr Asn Leu Pro
            820                 825                 830
```

```
Ile Gly Gln Ala Asp Glu Met Gln Arg Tyr Val Glu Glu Asn Gln Thr
        835                 840                 845

Arg Asn Lys His Ile Asn Pro Asn Glu Trp Trp Lys Val Tyr Pro Ser
    850                 855                 860

Ser Val Thr Glu Phe Lys Phe Leu Phe Val Ser Gly His Phe Lys Gly
865                 870                 875                 880

Asn Tyr Lys Ala Gln Leu Thr Arg Leu Asn His Ile Thr Asn Cys Asn
                885                 890                 895

Gly Ala Val Leu Ser Val Glu Glu Leu Leu Ile Gly Gly Glu Met Ile
            900                 905                 910

Lys Ala Gly Thr Leu Thr Leu Glu Glu Val Arg Arg Lys Phe Asn Asn
        915                 920                 925

Gly Glu Ile Asn Phe Ala Ala Asp
    930                 935


<210> SEQ ID NO 9
<211> LENGTH: 2814
<212> TYPE: DNA
<213> ORGANISM: Artificial sequence
<220> FEATURE:
<223> OTHER INFORMATION: Description of artificial sequence: Synthetic
      polynucleotide
<220> FEATURE:
<223> OTHER INFORMATION: pCLS9984

<400> SEQUENCE: 9

atgggcgatc ctaaaaagaa acgtaaggtc atcgattacc catacgatgt tccagattac      60

gctatcgata tcgccgatct acgcacgctc ggctacagcc agcagcaaca ggagaagatc     120

aaaccgaagg ttcgttcgac agtggcgcag caccacgagg cactggtcgg ccacgggttt     180

acacacgcgc acatcgttgc gttaagccaa cacccggcag cgttagggac cgtcgctgtc     240

aagtatcagg acatgatcgc agcgttgcca gaggcgacac acgaagcgat cgttggcgtc     300

ggcaaacagt ggtccggcgc acgcgctctg gaggccttgc tcacggtggc gggagagttg     360

agaggtccac cgttacagtt ggacacaggc caacttctca agattgcaaa acgtggcggc     420

gtgaccgcag tggaggcagt gcatgcatgg cgcaatgcac tgacgggtgc cccgctcaac     480

ttgacccccc agcaggtggt ggccatcgcc agcaatggcg gtggcaagca ggcgctggag     540

acggtccagc ggctgttgcc ggtgctgtgc caggcccacg gcttgacccc ggagcaggtg     600

gtggccatcg ccagccacga tggcggcaag caggcgctgg agacggtcca gcggctgttg     660

ccggtgctgt gccaggccca cggcttgacc ccccagcagg tggtggccat cgccagcaat     720

aatggtggca agcaggcgct ggagacggtc cagcggctgt tgccggtgct gtgccaggcc     780

cacggcttga ccccggagca ggtggtggcc atcgccagcc acgatggcgg caagcaggcg     840

ctggagacgg tccagcggct gttgccggtg ctgtgccagg cccacggctt gacccccag      900

caggtggtgg ccatcgccag caatggcggt ggcaagcagg cgctggagac ggtccagcgg     960

ctgttgccgg tgctgtgcca ggcccacggc ttgacccccc agcaggtggt ggccatcgcc    1020

agcaataatg gtggcaagca ggcgctggag acggtccagc ggctgttgcc ggtgctgtgc    1080

caggcccacg gcttgacccc ggagcaggtg gtggccatcg ccagccacga tggcggcaag    1140

caggcgctgg agacggtcca gcggctgttg ccggtgctgt gccaggccca cggcttgacc    1200

ccggagcagg tggtggccat cgccagcaat attggtggca agcaggcgct ggagacggtg    1260

caggcgctgt tgccggtgct gtgccaggcc cacggcttga cccccagca ggtggtggcc    1320
```

-continued

```
atcgccagca ataatggtgg caagcaggcg ctggagacgg tccagcggct gttgccggtg   1380

ctgtgccagg cccacggctt gaccccggag caggtggtgg ccatcgccag ccacgatggc   1440

ggcaagcagg cgctggagac ggtccagcgg ctgttgccgg tgctgtgcca ggcccacggc   1500

ttgaccccgg agcaggtggt ggccatcgcc agcaatattg gtggcaagca ggcgctggag   1560

acggtgcagg cgctgttgcc ggtgctgtgc caggcccacg gcttgacccc ccagcaggtg   1620

gtggccatcg ccagcaataa tggtggcaag caggcgctgg agacggtcca gcggctgttg   1680

ccggtgctgt gccaggccca cggcttgacc ccggagcagg tggtggccat cgccagccac   1740

gatggcggca agcaggcgct ggagacggtc cagcggctgt tgccggtgct gtgccaggcc   1800

cacggcttga ccccggagca ggtggtggcc atcgccagca atattggtgg caagcaggcg   1860

ctggagacgg tgcaggcgct gttgccggtg ctgtgccagg cccacggctt gaccccccag   1920

caggtggtgg ccatcgccag caataatggt ggcaagcagg cgctggagac ggtccagcgg   1980

ctgttgccgg tgctgtgcca ggcccacggc ttgacccctc agcaggtggt ggccatcgcc   2040

agcaatggcg gcggcaggcc ggcgctggag agcattgttg cccagttatc tcgccctgat   2100

ccggcgttgg ccgcgttgac caacgaccac ctcgtcgcct tggcctgcct cggcgggcgt   2160

cctgcgctgg atgcagtgaa aaagggattg gggatcccta tcagccgttc ccagctggtg   2220

aagtccgagc tggaggagaa gaaatccgag ttgaggcaca agctgaagta cgtgccccac   2280

gagtacatcg agctgatcga gatcgcccgg aacagcaccc aggaccgtat cctggagatg   2340

aaggtgatgg agttcttcat gaaggtgtac ggctacaggg gcaagcacct gggcggctcc   2400

aggaagcccg acggcgccat ctacaccgtg ggctccccca tcgactacgg cgtgatcgtg   2460

gacaccaagg cctactccgg cggctacaac ctgcccatcg gccaggccga cgaaatgcag   2520

aggtacgtgg aggagaacca gaccaggaac aagcacatca accccaacga gtggtggaag   2580

gtgtacccct ccagcgtgac cgagttcaag ttcctgttcg tgtccggcca cttcaagggc   2640

aactacaagg cccagctgac caggctgaac cacatcacca actgcaacgg cgccgtgctg   2700

tccgtggagg agctcctgat cggcggcgag atgatcaagg ccggcaccct gaccctggag   2760

gaggtgagga ggaagttcaa caacggcgag atcaacttcg cggccgactg ataa         2814
```

<210> SEQ ID NO 10
<211> LENGTH: 936
<212> TYPE: PRT
<213> ORGANISM: Artificial sequence
<220> FEATURE:
<223> OTHER INFORMATION: Description of artificial sequence: Synthetic polypeptide
<220> FEATURE:
<223> OTHER INFORMATION: pCLS16715

<400> SEQUENCE: 10

```
Met Gly Asp Pro Lys Lys Lys Arg Lys Val Ile Asp Tyr Pro Tyr Asp
1               5                   10                  15

Val Pro Asp Tyr Ala Ile Asp Ile Ala Asp Leu Arg Thr Leu Gly Tyr
            20                  25                  30

Ser Gln Gln Gln Gln Glu Lys Ile Lys Pro Lys Val Arg Ser Thr Val
        35                  40                  45

Ala Gln His His Glu Ala Leu Val Gly His Gly Phe Thr His Ala His
    50                  55                  60

Ile Val Ala Leu Ser Gln His Pro Ala Ala Leu Gly Thr Val Ala Val
65                  70                  75                  80

Lys Tyr Gln Asp Met Ile Ala Ala Leu Pro Glu Ala Thr His Glu Ala
```

```
                85                  90                  95

Ile Val Gly Val Gly Lys Gln Trp Ser Gly Ala Arg Ala Leu Glu Ala
            100                 105                 110

Leu Leu Thr Val Ala Gly Glu Leu Arg Gly Pro Pro Leu Gln Leu Asp
        115                 120                 125

Thr Gly Gln Leu Leu Lys Ile Ala Lys Arg Gly Gly Val Thr Ala Val
    130                 135                 140

Glu Ala Val His Ala Trp Arg Asn Ala Leu Thr Gly Ala Pro Leu Asn
145                 150                 155                 160

Leu Thr Pro Gln Gln Val Val Ala Ile Ala Ser Asn Asn Gly Gly Lys
                165                 170                 175

Gln Ala Leu Glu Thr Val Gln Arg Leu Leu Pro Val Leu Cys Gln Ala
            180                 185                 190

His Gly Leu Thr Pro Gln Gln Val Val Ala Ile Ala Ser Asn Gly Gly
        195                 200                 205

Gly Lys Gln Ala Leu Glu Thr Val Gln Arg Leu Leu Pro Val Leu Cys
    210                 215                 220

Gln Ala His Gly Leu Thr Pro Gln Gln Val Val Ala Ile Ala Ser Asn
225                 230                 235                 240

Asn Gly Gly Lys Gln Ala Leu Glu Thr Val Gln Arg Leu Leu Pro Val
                245                 250                 255

Leu Cys Gln Ala His Gly Leu Thr Pro Glu Gln Val Val Ala Ile Ala
            260                 265                 270

Ser Asn Ile Gly Gly Lys Gln Ala Leu Glu Thr Val Gln Ala Leu Leu
        275                 280                 285

Pro Val Leu Cys Gln Ala His Gly Leu Thr Pro Gln Gln Val Val Ala
    290                 295                 300

Ile Ala Ser Asn Gly Gly Gly Lys Gln Ala Leu Glu Thr Val Gln Arg
305                 310                 315                 320

Leu Leu Pro Val Leu Cys Gln Ala His Gly Leu Thr Pro Glu Gln Val
                325                 330                 335

Val Ala Ile Ala Ser His Asp Gly Gly Lys Gln Ala Leu Glu Thr Val
            340                 345                 350

Gln Arg Leu Leu Pro Val Leu Cys Gln Ala His Gly Leu Thr Pro Glu
        355                 360                 365

Gln Val Val Ala Ile Ala Ser His Asp Gly Gly Lys Gln Ala Leu Glu
    370                 375                 380

Thr Val Gln Arg Leu Leu Pro Val Leu Cys Gln Ala His Gly Leu Thr
385                 390                 395                 400

Pro Glu Gln Val Val Ala Ile Ala Ser His Asp Gly Gly Lys Gln Ala
                405                 410                 415

Leu Glu Thr Val Gln Arg Leu Leu Pro Val Leu Cys Gln Ala His Gly
            420                 425                 430

Leu Thr Pro Glu Gln Val Val Ala Ile Ala Ser His Asp Gly Gly Lys
        435                 440                 445

Gln Ala Leu Glu Thr Val Gln Arg Leu Leu Pro Val Leu Cys Gln Ala
    450                 455                 460

His Gly Leu Thr Pro Glu Gln Val Val Ala Ile Ala Ser His Asp Gly
465                 470                 475                 480

Gly Lys Gln Ala Leu Glu Thr Val Gln Arg Leu Leu Pro Val Leu Cys
                485                 490                 495

Gln Ala His Gly Leu Thr Pro Glu Gln Val Val Ala Ile Ala Ser His
            500                 505                 510
```

```
Asp Gly Gly Lys Gln Ala Leu Glu Thr Val Gln Arg Leu Leu Pro Val
        515                 520                 525

Leu Cys Gln Ala His Gly Leu Thr Pro Glu Gln Val Val Ala Ile Ala
    530                 535                 540

Ser Asn Ile Gly Gly Lys Gln Ala Leu Glu Thr Val Gln Ala Leu Leu
545                 550                 555                 560

Pro Val Leu Cys Gln Ala His Gly Leu Thr Pro Gln Gln Val Val Ala
                565                 570                 575

Ile Ala Ser Asn Asn Gly Gly Lys Gln Ala Leu Glu Thr Val Gln Arg
            580                 585                 590

Leu Leu Pro Val Leu Cys Gln Ala His Gly Leu Thr Pro Glu Gln Val
        595                 600                 605

Val Ala Ile Ala Ser His Asp Gly Gly Lys Gln Ala Leu Glu Thr Val
    610                 615                 620

Gln Arg Leu Leu Pro Val Leu Cys Gln Ala His Gly Leu Thr Pro Glu
625                 630                 635                 640

Gln Val Val Ala Ile Ala Ser Asn Ile Gly Gly Lys Gln Ala Leu Glu
                645                 650                 655

Thr Val Gln Ala Leu Leu Pro Val Leu Cys Gln Ala His Gly Leu Thr
            660                 665                 670

Pro Gln Gln Val Val Ala Ile Ala Ser Asn Gly Gly Gly Arg Pro Ala
        675                 680                 685

Leu Glu Ser Ile Val Ala Gln Leu Ser Arg Pro Asp Pro Ala Leu Ala
    690                 695                 700

Ala Leu Thr Asn Asp His Leu Val Ala Leu Ala Cys Leu Gly Gly Arg
705                 710                 715                 720

Pro Ala Leu Asp Ala Val Lys Lys Gly Leu Gly Asp Pro Ile Ser Arg
                725                 730                 735

Ser Gln Leu Val Lys Ser Glu Leu Glu Glu Lys Lys Ser Glu Leu Arg
            740                 745                 750

His Lys Leu Lys Tyr Val Pro His Glu Tyr Ile Glu Leu Ile Glu Ile
        755                 760                 765

Ala Arg Asn Ser Thr Gln Asp Arg Ile Leu Glu Met Lys Val Met Glu
    770                 775                 780

Phe Phe Met Lys Val Tyr Gly Tyr Arg Gly Lys His Leu Gly Gly Ser
785                 790                 795                 800

Arg Lys Pro Asp Gly Ala Ile Tyr Thr Val Gly Ser Pro Ile Asp Tyr
                805                 810                 815

Gly Val Ile Val Asp Thr Lys Ala Tyr Ser Gly Gly Tyr Asn Leu Pro
            820                 825                 830

Ile Gly Gln Ala Asp Glu Met Gln Arg Tyr Val Glu Glu Asn Gln Thr
        835                 840                 845

Arg Asn Lys His Ile Asn Pro Asn Glu Trp Trp Lys Val Tyr Pro Ser
    850                 855                 860

Ser Val Thr Glu Phe Lys Phe Leu Phe Val Ser Gly His Phe Lys Gly
865                 870                 875                 880

Asn Tyr Lys Ala Gln Leu Thr Arg Leu Asn His Ile Thr Asn Cys Asn
                885                 890                 895

Gly Ala Val Leu Ser Val Glu Glu Leu Leu Ile Gly Gly Glu Met Ile
            900                 905                 910

Lys Ala Gly Thr Leu Thr Leu Glu Glu Val Arg Arg Lys Phe Asn Asn
        915                 920                 925
```

```
Gly Glu Ile Asn Phe Ala Ala Asp
    930                 935


<210> SEQ ID NO 11
<211> LENGTH: 2814
<212> TYPE: DNA
<213> ORGANISM: Artificial sequence
<220> FEATURE:
<223> OTHER INFORMATION: Description of artificial sequence: Synthetic
      polynucleotide
<220> FEATURE:
<223> OTHER INFORMATION: pCLS16715

<400> SEQUENCE: 11

atgggcgatc ctaaaaagaa acgtaaggtc atcgattacc catacgatgt tccagattac     60

gctatcgata tcgccgatct acgcacgctc ggctacagcc agcagcaaca ggagaagatc    120

aaaccgaagg ttcgttcgac agtggcgcag caccacgagg cactggtcgg ccacgggttt    180

acacacgcgc acatcgttgc gttaagccaa cacccggcag cgttagggac cgtcgctgtc    240

aagtatcagg acatgatcgc agcgttgcca gaggcgacac acgaagcgat cgttggcgtc    300

ggcaaacagt ggtccggcgc acgcgctctg gaggccttgc tcacggtggc gggagagttg    360

agaggtccac cgttacagtt ggacacaggc caacttctca agattgcaaa acgtggcggc    420

gtgaccgcag tggaggcagt gcatgcatgg cgcaatgcac tgacgggtgc cccgctcaac    480

ttgacccccc agcaggtggt ggccatcgcc agcaataatg gtggcaagca ggcgctggag    540

acggtccagc ggctgttgcc ggtgctgtgc caggcccacg gcttgacccc ccagcaggtg    600

gtggccatcg ccagcaatgg cggtggcaag caggcgctgg agacggtcca gcggctgttg    660

ccggtgctgt gccaggccca cggcttgacc ccccagcagg tggtggccat cgccagcaat    720

aatggtggca agcaggcgct ggagacggtc cagcggctgt tgccggtgct gtgccaggcc    780

cacggcttga ccccggagca ggtggtggcc atcgccagca atattggtgg caagcaggcg    840

ctggagacgg tgcaggcgct gttgccggtg ctgtgccagg cccacggctt gacccccccag    900

caggtggtgg ccatcgccag caatggcggt ggcaagcagg cgctggagac ggtccagcgg    960

ctgttgccgg tgctgtgcca ggcccacggc ttgaccccgg agcaggtggt ggccatcgcc   1020

agccacgatg gcggcaagca ggcgctggag acggtccagc ggctgttgcc ggtgctgtgc   1080

caggcccacg gcttgacccc ggagcaggtg gtggccatcg ccagccacga tggcggcaag   1140

caggcgctgg agacggtcca gcggctgttg ccggtgctgt gccaggccca cggcttgacc   1200

ccggagcagg tggtggccat cgccagccac gatggcggca agcaggcgct ggagacggtc   1260

cagcggctgt tgccggtgct gtgccaggcc cacggcttga ccccggagca ggtggtggcc   1320

atcgccagcc acgatggcgg caagcaggcg ctggagacgg tccagcggct gttgccggtg   1380

ctgtgccagg cccacggctt gaccccggag caggtggtgg ccatcgccag ccacgatggc   1440

ggcaagcagg cgctggagac ggtccagcgg ctgttgccgg tgctgtgcca ggcccacggc   1500

ttgaccccgg agcaggtggt ggccatcgcc agccacgatg gcggcaagca ggcgctggag   1560

acggtccagc ggctgttgcc ggtgctgtgc caggcccacg gcttgacccc ggagcaggtg   1620

gtggccatcg ccagcaatat tggtggcaag caggcgctgg agacggtgca ggcgctgttg   1680

ccggtgctgt gccaggccca cggcttgacc ccccagcagg tggtggccat cgccagcaat   1740

aatggtggca agcaggcgct ggagacggtc cagcggctgt tgccggtgct gtgccaggcc   1800

cacggcttga ccccggagca ggtggtggcc atcgccagcc acgatggcgg caagcaggcg   1860

ctggagacgg tccagcggct gttgccggtg ctgtgccagg cccacggctt gaccccggag   1920
```

```
caggtggtgg ccatcgccag caatattggt ggcaagcagg cgctggagac ggtgcaggcg   1980

ctgttgccgg tgctgtgcca ggcccacggc ttgacccctc agcaggtggt ggccatcgcc   2040

agcaatggcg gcggcaggcc ggcgctggag agcattgttg cccagttatc tcgccctgat   2100

ccggcgttgg ccgcgttgac caacgaccac ctcgtcgcct tggcctgcct cggcgggcgt   2160

cctgcgctgg atgcagtgaa aaagggattg gggatcctta tcagccgttc ccagctggtg   2220

aagtccgagc tggaggagaa gaaatccgag ttgaggcaca agctgaagta cgtgccccac   2280

gagtacatcg agctgatcga gatcgcccgg aacagcaccc aggaccgtat cctggagatg   2340

aaggtgatgg agttcttcat gaaggtgtac ggctacaggg gcaagcacct gggcggctcc   2400

aggaagcccg acggcgccat ctacaccgtg ggctccccca tcgactacgg cgtgatcgtg   2460

gacaccaagg cctactccgg cggctacaac ctgcccatcg gccaggccga cgaaatgcag   2520

aggtacgtgg aggagaacca gaccaggaac aagcacatca accccaacga gtggtggaag   2580

gtgtacccct ccagcgtgac cgagttcaag ttcctgttcg tgtccggcca cttcaagggc   2640

aactacaagg cccagctgac caggctgaac cacatcacca actgcaacgg cgccgtgctg   2700

tccgtggagg agctcctgat cggcggcgag atgatcaagg ccggcaccct gaccctggag   2760

gaggtgagga ggaagttcaa caacggcgag atcaacttcg cggccgactg ataa         2814
```

```
<210> SEQ ID NO 12
<211> LENGTH: 69
<212> TYPE: DNA
<213> ORGANISM: Artificial sequence
<220> FEATURE:
<223> OTHER INFORMATION: Description of artificial sequence: Synthetic
      polynucleotide
<220> FEATURE:
<223> OTHER INFORMATION: TIFLAN

<400> SEQUENCE: 12

tctcaagatt tcgctgcagc agcagcagca gcagcagcag cagcagcagc agcagcagca     60

gcagcagca                                                             69


<210> SEQ ID NO 13
<211> LENGTH: 46
<212> TYPE: DNA
<213> ORGANISM: Artificial sequence
<220> FEATURE:
<223> OTHER INFORMATION: Description of artificial sequence: Synthetic
      polynucleotide
<220> FEATURE:
<223> OTHER INFORMATION: TIFLAN2

<400> SEQUENCE: 13

tgtgatcccc ccagcagcag cagcagcagc agcagcagca gcagca                    46


<210> SEQ ID NO 14
<211> LENGTH: 530
<212> TYPE: PRT
<213> ORGANISM: Artificial sequence
<220> FEATURE:
<223> OTHER INFORMATION: Description of artificial sequence: Synthetic
      polypeptide
<220> FEATURE:
<223> OTHER INFORMATION: TiCAG

<400> SEQUENCE: 14

Leu Thr Pro Gln Gln Val Val Ala Ile Ala Ser Asn Asn Gly Gly Lys
1               5                   10                  15
```

```
Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
            100                 105                 110

Ser Asn Asn Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Gly Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Asn Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
            260                 265                 270

Leu Thr Pro Gln Gln Val Val Ala Ile Ala Ser Asn Gly Gly Gly Lys
        275                 280                 285

Gln Ala Leu Glu Thr Val Gln Arg Leu Leu Pro Val Leu Cys Gln Ala
    290                 295                 300

His Gly Leu Thr Pro Gln Gln Val Val Ala Ile Ala Ser Asn Asn Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser His
            340                 345                 350

Asp Gly Gly Lys Gln Ala Leu Glu Thr Val Gln Arg Leu Leu Pro Val
        355                 360                 365

Leu Cys Gln Ala His Gly Leu Thr Pro Gln Gln Val Val Ala Ile Ala
    370                 375                 380

Ser Asn Gly Gly Gly Lys Gln Ala Leu Glu Thr Val Gln Arg Leu Leu
385                 390                 395                 400

Pro Val Leu Cys Gln Ala His Gly Leu Thr Pro Gln Gln Val Val Ala
                405                 410                 415

Ile Ala Ser Asn Asn Gly Gly Lys Gln Ala Leu Glu Thr Val Gln Arg
            420                 425                 430

Leu Leu Pro Val Leu Cys Gln Ala His Gly Leu Thr Pro Glu Gln Val
```

```
        435                 440                 445

Val Ala Ile Ala Ser His Asp Gly Gly Lys Gln Ala Leu Glu Thr Val
    450                 455                 460

Gln Arg Leu Leu Pro Val Leu Cys Gln Ala His Gly Leu Thr Pro Gln
465                 470                 475                 480

Gln Val Val Ala Ile Ala Ser Asn Gly Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530


<210> SEQ ID NO 15
<211> LENGTH: 942
<212> TYPE: PRT
<213> ORGANISM: Artificial sequence
<220> FEATURE:
<223> OTHER INFORMATION: Description of artificial sequence: Synthetic
      polypeptide
<220> FEATURE:
<223> OTHER INFORMATION: pCLS9996

<400> SEQUENCE: 15

Met Gly Asp Pro Lys Lys Lys Arg Lys Val Ile Asp Lys Glu Thr Ala
1               5                   10                  15

Ala Ala Lys Phe Glu Arg Gln His Met Asp Ser Ile Asp Ile Ala Asp
            20                  25                  30

Leu Arg Thr Leu Gly Tyr Ser Gln Gln Gln Gln Glu Lys Ile Lys Pro
        35                  40                  45

Lys Val Arg Ser Thr Val Ala Gln His His Glu Ala Leu Val Gly His
    50                  55                  60

Gly Phe Thr His Ala His Ile Val Ala Leu Ser Gln His Pro Ala Ala
65                  70                  75                  80

Leu Gly Thr Val Ala Val Lys Tyr Gln Asp Met Ile Ala Ala Leu Pro
                85                  90                  95

Glu Ala Thr His Glu Ala Ile Val Gly Val Gly Lys Gln Trp Ser Gly
            100                 105                 110

Ala Arg Ala Leu Glu Ala Leu Leu Thr Val Ala Gly Glu Leu Arg Gly
        115                 120                 125

Pro Pro Leu Gln Leu Asp Thr Gly Gln Leu Leu Lys Ile Ala Lys Arg
    130                 135                 140

Gly Gly Val Thr Ala Val Glu Ala Val His Ala Trp Arg Asn Ala Leu
145                 150                 155                 160

Thr Gly Ala Pro Leu Asn Leu Thr Pro Gln Gln Val Val Ala Ile Ala
                165                 170                 175

Ser Asn Asn Gly Gly Lys Gln Ala Leu Glu Thr Val Gln Arg Leu Leu
            180                 185                 190

Pro Val Leu Cys Gln Ala His Gly Leu Thr Pro Glu Gln Val Val Ala
        195                 200                 205

Ile Ala Ser His Asp Gly Gly Lys Gln Ala Leu Glu Thr Val Gln Arg
    210                 215                 220

Leu Leu Pro Val Leu Cys Gln Ala His Gly Leu Thr Pro Gln Gln Val
225                 230                 235                 240

Val Ala Ile Ala Ser Asn Gly Gly Gly Lys Gln Ala Leu Glu Thr Val
```

-continued

```
                245                 250                 255

Gln Arg Leu Leu Pro Val Leu Cys Gln Ala His Gly Leu Thr Pro Gln
            260                 265                 270

Gln Val Val Ala Ile Ala Ser Asn Asn Gly Gly Lys Gln Ala Leu Glu
        275                 280                 285

Thr Val Gln Arg Leu Leu Pro Val Leu Cys Gln Ala His Gly Leu Thr
    290                 295                 300

Pro Glu Gln Val Val Ala Ile Ala Ser His Asp Gly Gly Lys Gln Ala
305                 310                 315                 320

Leu Glu Thr Val Gln Arg Leu Leu Pro Val Leu Cys Gln Ala His Gly
                325                 330                 335

Leu Thr Pro Gln Gln Val Val Ala Ile Ala Ser Asn Gly Gly Gly Lys
            340                 345                 350

Gln Ala Leu Glu Thr Val Gln Arg Leu Leu Pro Val Leu Cys Gln Ala
        355                 360                 365

His Gly Leu Thr Pro Gln Gln Val Val Ala Ile Ala Ser Asn Asn Gly
    370                 375                 380

Gly Lys Gln Ala Leu Glu Thr Val Gln Arg Leu Leu Pro Val Leu Cys
385                 390                 395                 400

Gln Ala His Gly Leu Thr Pro Glu Gln Val Val Ala Ile Ala Ser His
                405                 410                 415

Asp Gly Gly Lys Gln Ala Leu Glu Thr Val Gln Arg Leu Leu Pro Val
            420                 425                 430

Leu Cys Gln Ala His Gly Leu Thr Pro Gln Gln Val Val Ala Ile Ala
        435                 440                 445

Ser Asn Gly Gly Gly Lys Gln Ala Leu Glu Thr Val Gln Arg Leu Leu
    450                 455                 460

Pro Val Leu Cys Gln Ala His Gly Leu Thr Pro Gln Gln Val Val Ala
465                 470                 475                 480

Ile Ala Ser Asn Asn Gly Gly Lys Gln Ala Leu Glu Thr Val Gln Arg
                485                 490                 495

Leu Leu Pro Val Leu Cys Gln Ala His Gly Leu Thr Pro Glu Gln Val
            500                 505                 510

Val Ala Ile Ala Ser His Asp Gly Gly Lys Gln Ala Leu Glu Thr Val
        515                 520                 525

Gln Arg Leu Leu Pro Val Leu Cys Gln Ala His Gly Leu Thr Pro Gln
    530                 535                 540

Gln Val Val Ala Ile Ala Ser Asn Gly Gly Gly Lys Gln Ala Leu Glu
545                 550                 555                 560

Thr Val Gln Arg Leu Leu Pro Val Leu Cys Gln Ala His Gly Leu Thr
                565                 570                 575

Pro Gln Gln Val Val Ala Ile Ala Ser Asn Asn Gly Gly Lys Gln Ala
            580                 585                 590

Leu Glu Thr Val Gln Arg Leu Leu Pro Val Leu Cys Gln Ala His Gly
        595                 600                 605

Leu Thr Pro Glu Gln Val Val Ala Ile Ala Ser His Asp Gly Gly Lys
    610                 615                 620

Gln Ala Leu Glu Thr Val Gln Arg Leu Leu Pro Val Leu Cys Gln Ala
625                 630                 635                 640

His Gly Leu Thr Pro Gln Gln Val Val Ala Ile Ala Ser Asn Gly Gly
                645                 650                 655

Gly Lys Gln Ala Leu Glu Thr Val Gln Arg Leu Leu Pro Val Leu Cys
            660                 665                 670
```

```
Gln Ala His Gly Leu Thr Pro Gln Gln Val Val Ala Ile Ala Ser Asn
        675                 680                 685

Gly Gly Gly Arg Pro Ala Leu Glu Ser Ile Val Ala Gln Leu Ser Arg
    690                 695                 700

Pro Asp Pro Ala Leu Ala Ala Leu Thr Asn Asp His Leu Val Ala Leu
705                 710                 715                 720

Ala Cys Leu Gly Gly Arg Pro Ala Leu Asp Ala Val Lys Lys Gly Leu
                725                 730                 735

Gly Asp Pro Ile Ser Arg Ser Gln Leu Val Lys Ser Glu Leu Glu Glu
            740                 745                 750

Lys Lys Ser Glu Leu Arg His Lys Leu Lys Tyr Val Pro His Glu Tyr
        755                 760                 765

Ile Glu Leu Ile Glu Ile Ala Arg Asn Ser Thr Gln Asp Arg Ile Leu
    770                 775                 780

Glu Met Lys Val Met Glu Phe Phe Met Lys Val Tyr Gly Tyr Arg Gly
785                 790                 795                 800

Lys His Leu Gly Gly Ser Arg Lys Pro Asp Gly Ala Ile Tyr Thr Val
                805                 810                 815

Gly Ser Pro Ile Asp Tyr Gly Val Ile Val Asp Thr Lys Ala Tyr Ser
            820                 825                 830

Gly Gly Tyr Asn Leu Pro Ile Gly Gln Ala Asp Glu Met Gln Arg Tyr
        835                 840                 845

Val Glu Glu Asn Gln Thr Arg Asn Lys His Ile Asn Pro Asn Glu Trp
    850                 855                 860

Trp Lys Val Tyr Pro Ser Ser Val Thr Glu Phe Lys Phe Leu Phe Val
865                 870                 875                 880

Ser Gly His Phe Lys Gly Asn Tyr Lys Ala Gln Leu Thr Arg Leu Asn
                885                 890                 895

His Ile Thr Asn Cys Asn Gly Ala Val Leu Ser Val Glu Glu Leu Leu
            900                 905                 910

Ile Gly Gly Glu Met Ile Lys Ala Gly Thr Leu Thr Leu Glu Glu Val
        915                 920                 925

Arg Arg Lys Phe Asn Asn Gly Glu Ile Asn Phe Ala Ala Asp
    930                 935                 940
```

<210> SEQ ID NO 16
<211> LENGTH: 2832
<212> TYPE: DNA
<213> ORGANISM: Artificial sequence
<220> FEATURE:
<223> OTHER INFORMATION: Description of artificial sequence: Synthetic polynucleotide
<220> FEATURE:
<223> OTHER INFORMATION: pCLS9996

<400> SEQUENCE: 16

```
atgggcgatc ctaaaaagaa acgtaaggtc atcgataagg agaccgccgc tgccaagttc      60

gagagacagc acatggacag catcgatatc gccgatctac gcacgctcgg ctacagccag     120

cagcaacagg agaagatcaa accgaaggtt cgttcgacag tggcgcagca ccacgaggca     180

ctggtcggcc acgggtttac acacgcgcac atcgttgcgt taagccaaca cccggcagcg     240

ttagggaccg tcgctgtcaa gtatcaggac atgatcgcag cgttgccaga ggcgacacac     300

gaagcgatcg ttggcgtcgg caaacagtgg tccggcgcac gcgctctgga ggccttgctc     360

acggtggcgg gagagttgag aggtccaccg ttacagttgg acacaggcca acttctcaag     420
```

-continued

```
attgcaaaac gtggcggcgt gaccgcagtg gaggcagtgc atgcatggcg caatgcactg    480
acgggtgccc cgctcaactt gaccccccag caggtggtgg ccatcgccag caataatggt    540
ggcaagcagg cgctggagac ggtccagcgg ctgttgccgg tgctgtgcca ggcccacggc    600
ttgaccccgg agcaggtggt ggccatcgcc agccacgatg gcggcaagca ggcgctggag    660
acggtccagc ggctgttgcc ggtgctgtgc caggcccacg gcttgacccc ccagcaggtg    720
gtggccatcg ccagcaatgg cggtggcaag caggcgctgg agacggtcca gcggctgttg    780
ccggtgctgt gccaggccca cggcttgacc ccccagcagg tggtggccat cgccagcaat    840
aatggtggca agcaggcgct ggagacggtc cagcggctgt tgccggtgct gtgccaggcc    900
cacggcttga ccccggagca ggtggtggcc atcgccagcc acgatggcgg caagcaggcg    960
ctggagacgg tccagcggct gttgccggtg ctgtgccagg cccacggctt gaccccccag   1020
caggtggtgg ccatcgccag caatggcggt ggcaagcagg cgctggagac ggtccagcgg   1080
ctgttgccgg tgctgtgcca ggcccacggc ttgacccccc agcaggtggt ggccatcgcc   1140
agcaataatg gtggcaagca ggcgctggag acggtccagc ggctgttgcc ggtgctgtgc   1200
caggcccacg gcttgacccc ggagcaggtg gtggccatcg ccagccacga tggcggcaag   1260
caggcgctgg agacggtcca gcggctgttg ccggtgctgt gccaggccca cggcttgacc   1320
ccccagcagg tggtggccat cgccagcaat ggcggtggca agcaggcgct ggagacggtc   1380
cagcggctgt tgccggtgct gtgccaggcc cacggcttga ccccccagca ggtggtggcc   1440
atcgccagca ataatggtgg caagcaggcg ctggagacgg tccagcggct gttgccggtg   1500
ctgtgccagg cccacggctt gaccccggag caggtggtgg ccatcgccag ccacgatggc   1560
ggcaagcagg cgctggagac ggtccagcgg ctgttgccgg tgctgtgcca ggcccacggc   1620
ttgacccccc agcaggtggt ggccatcgcc agcaatggcg gtggcaagca ggcgctggag   1680
acggtccagc ggctgttgcc ggtgctgtgc caggcccacg gcttgacccc ccagcaggtg   1740
gtggccatcg ccagcaataa tggtggcaag caggcgctgg agacggtcca gcggctgttg   1800
ccggtgctgt gccaggccca cggcttgacc ccggagcagg tggtggccat cgccagccac   1860
gatggcggca agcaggcgct ggagacggtc cagcggctgt tgccggtgct gtgccaggcc   1920
cacggcttga ccccccagca ggtggtggcc atcgccagca atggcggtgg caagcaggcg   1980
ctggagacgg tccagcggct gttgccggtg ctgtgccagg cccacggctt gacccctcag   2040
caggtggtgg ccatcgccag caatggcggc ggcaggccgg cgctggagag cattgttgcc   2100
cagttatctc gccctgatcc ggcgttggcc gcgttgacca acgaccacct cgtcgccttg   2160
gcctgcctcg gcgggcgtcc tgcgctggat gcagtgaaaa agggattggg ggatcctatc   2220
agccgttccc agctggtgaa gtccgagctg gaggagaaga aatccgagtt gaggcacaag   2280
ctgaagtacg tgccccacga gtacatcgag ctgatcgaga tcgcccggaa cagcacccag   2340
gaccgtatcc tggagatgaa ggtgatggag ttcttcatga aggtgtacgg ctacaggggc   2400
aagcacctgg gcggctccag gaagcccgac ggcgccatct acaccgtggg ctcccccatc   2460
gactacggcg tgatcgtgga caccaaggcc tactccggcg gctacaacct gcccatcggc   2520
caggccgacg aaatgcagag gtacgtggag gagaaccaga ccaggaacaa gcacatcaac   2580
cccaacgagt ggtggaaggt gtacccctcc agcgtgaccg agttcaagtt cctgttcgtg   2640
```

-continued

```
tccggccact tcaagggcaa ctacaaggcc cagctgacca ggctgaacca catcaccaac   2700

tgcaacggcg ccgtgctgtc cgtggaggag ctcctgatcg gcggcgagat gatcaaggcc   2760

ggcaccctga ccctggagga ggtgaggagg aagttcaaca acggcgagat caacttcgcg   2820

gccgactgat aa                                                       2832
```